US009968259B2

(12) United States Patent
Niedre et al.

(10) Patent No.: US 9,968,259 B2
(45) Date of Patent: May 15, 2018

(54) SYSTEMS AND METHODS FOR SENSING, ENUMERATING AND IMAGING RARE CELLS WITH DIFFUSE LIGHT

(71) Applicants: Mark Niedre, Roslindale, MA (US); Eric William Zettergren, Boston, MA (US); Charles P. Lin, Arlington, MA (US)

(72) Inventors: Mark Niedre, Roslindale, MA (US); Eric William Zettergren, Boston, MA (US); Charles P. Lin, Arlington, MA (US)

(73) Assignees: NORTHEASTERN UNIVERSITY, Boston, MA (US); THE GENERAL HOSPITAL CORPORATION, Boston, MA (US)

( * ) Notice: Subject to any disclaimer, the term of this patent is extended or adjusted under 35 U.S.C. 154(b) by 87 days.

(21) Appl. No.: 14/371,850

(22) PCT Filed: Jan. 24, 2013

(86) PCT No.: PCT/US2013/022927
§ 371 (c)(1),
(2) Date: Jul. 11, 2014

(87) PCT Pub. No.: WO2013/112709
PCT Pub. Date: Aug. 1, 2013

(65) Prior Publication Data
US 2014/0350394 A1    Nov. 27, 2014

Related U.S. Application Data

(60) Provisional application No. 61/590,178, filed on Jan. 24, 2012.

(51) Int. Cl.
A61B 5/00      (2006.01)
G01N 15/14    (2006.01)

(52) U.S. Cl.
CPC .......... *A61B 5/0071* (2013.01); *A61B 5/0073* (2013.01); *G01N 15/1404* (2013.01); *G01N 15/1434* (2013.01); *G01N 2015/1445* (2013.01)

(58) Field of Classification Search
CPC ................ A61B 5/0071; A61B 5/0073; G01N 15/1404; G01N 15/1434; G01N 2015/1445
See application file for complete search history.

(56) References Cited

U.S. PATENT DOCUMENTS 5,694,938 A  * 12/1997  Feng ..................... A61B 5/0073
                                                         600/425
6,615,063 B1 *  9/2003  Ntziachristos ....... A61B 5/0073
                                                         600/312

(Continued)

FOREIGN PATENT DOCUMENTS

JP      2006026017 A    2/2006
WO    WO-2009047328 A2  4/2009

OTHER PUBLICATIONS

Choe, Regine, "Diffuse Optical Tomography and Spectroscopy of Breast Cancer and Fetal Brain", Dissertation, University of Pennsylvania, URL: http://www.physics.upenn.edu/yodhlab/theses/regine_choe.pdf, Online Access Date: Oct. 2, 2016.*

(Continued)

*Primary Examiner* — Katherine Fernandez
(74) *Attorney, Agent, or Firm* — Morgan, Lewis & Bockius LLP

(57) ABSTRACT

Diffuse fluorescence flow cytometers and methods of using them include a plurality of excitation sources and a plurality of detectors, all circumferentially arranged about a space for accommodating a limb of a subject. Tomographic reconstructions of cells within the limb are made by varying the intensity and direction of excitation and then analyzing the results.

13 Claims, 16 Drawing Sheets

(56) References Cited

U.S. PATENT DOCUMENTS

2004/0197267 A1* 10/2004 Black .................. A61B 5/0071
424/9.6
2005/0228291 A1* 10/2005 Chance ............... A61B 5/0073
600/476
2011/0168871 A1* 7/2011 Gilbert .............. G01N 21/6452
250/208.1

OTHER PUBLICATIONS

Steinkamp et al., "Dual-Laser, Differential Fluorescence Correction Method for Reducing Cellular Background Autofluorescence", Cytometry, vol. 7, 1986, pp. 566-574.*
Niedre, M et al., "Comparison of fluorescence tomographic imaging in mice with early-arriving and quasi-continuous-wave photons", Optics Letters, OSA, Optical Society of America, vol. 35, No. 3, Feb. 1, 2010, pp. 369-371.
Niedre, M. et al., "Elucidating Structure and Function in Vivo with Hybrid Flouorescence and Magnetic Resonance Imaging", Proceedings of the IEEE, vol. 96, No. 3, Mar. 1, 2008, p. 382 and pp. 384-385.
Zettergren, Eric et al., "Validation of a device for fluorescence sensing of rare circulating cells with diffusive light in an optical flow phantom model", Engineering in Medicine and biology Society, EMBC, 2011 Annual International Conference of the IEEE, Aug. 30, 2011, pp. 486-489.
International Search Report dated Jan. 8, 2013 for International Application No. PCT/US2013/022927 (4 pages).

* cited by examiner

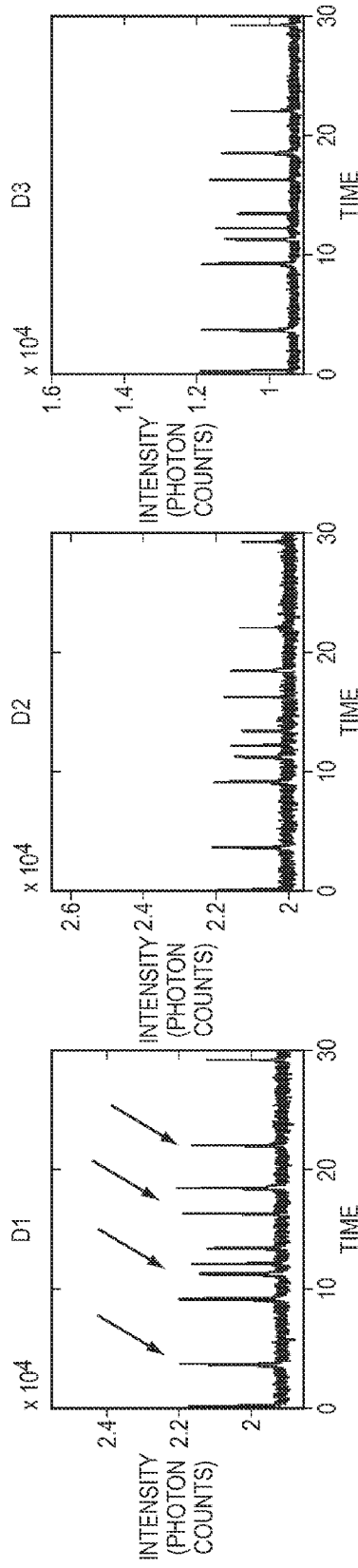
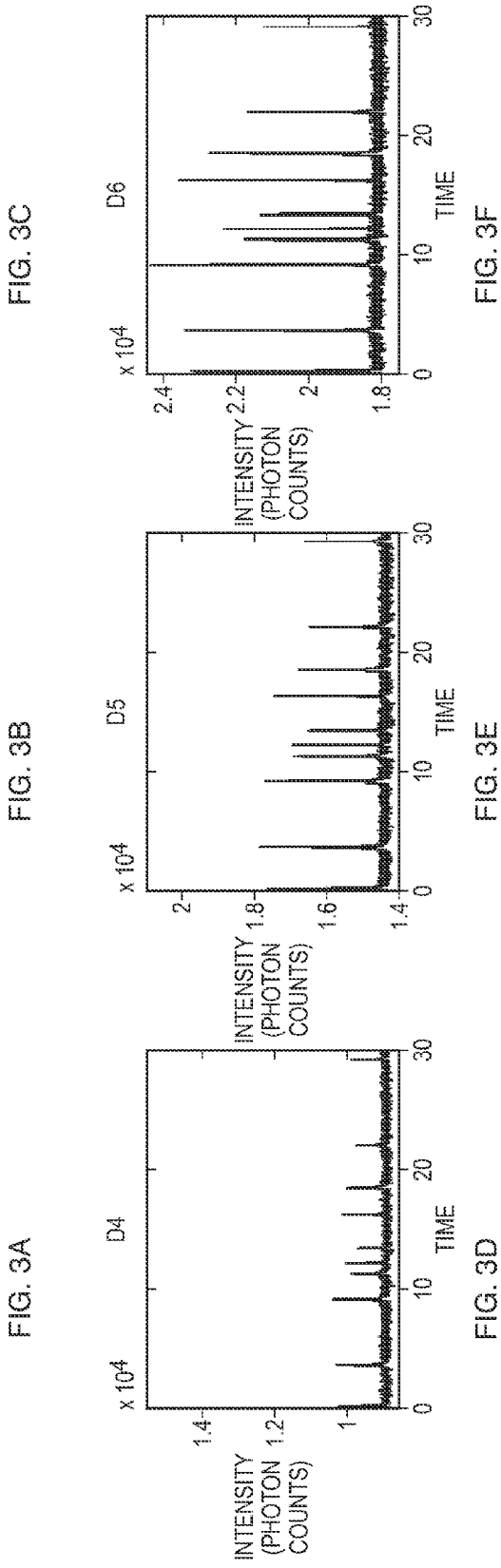

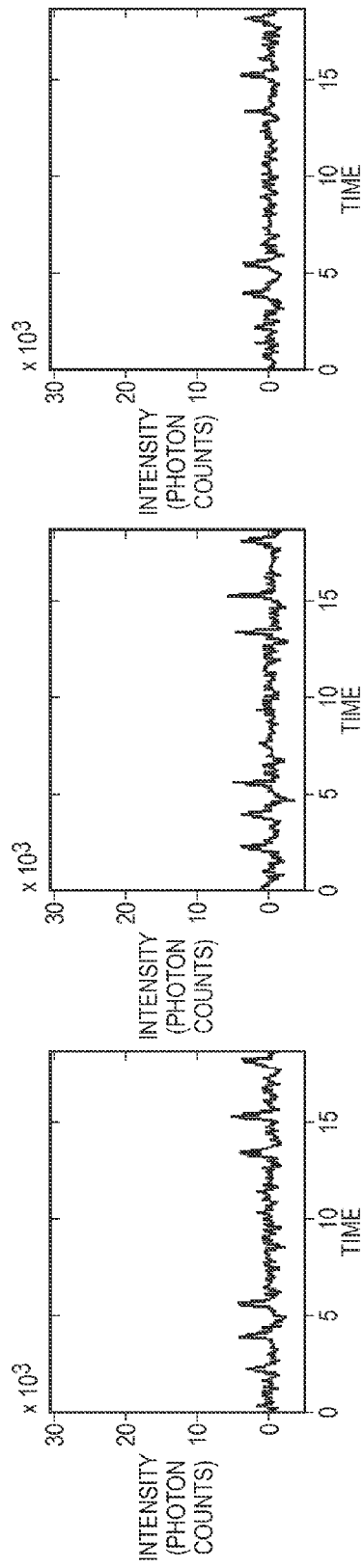
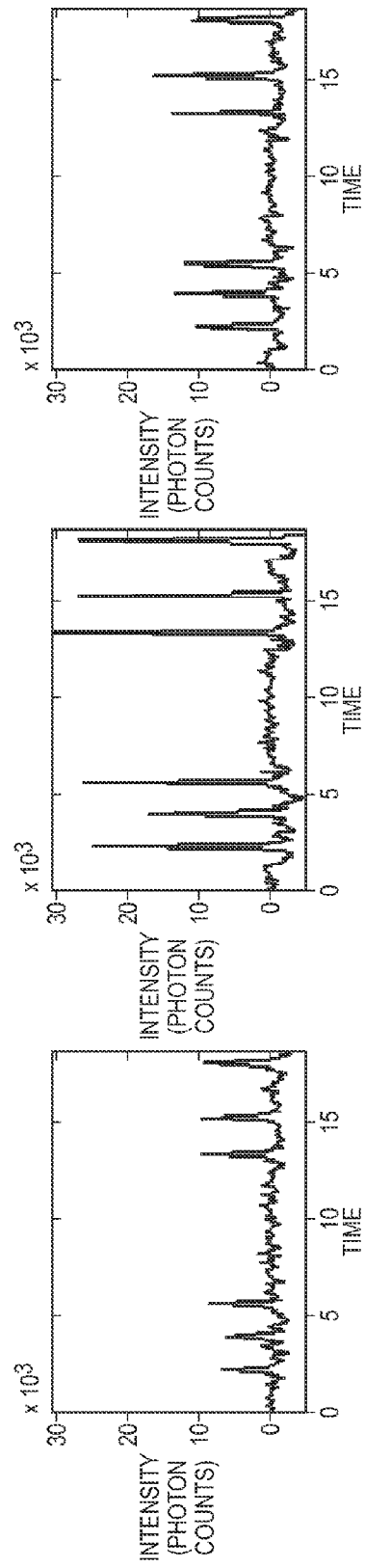

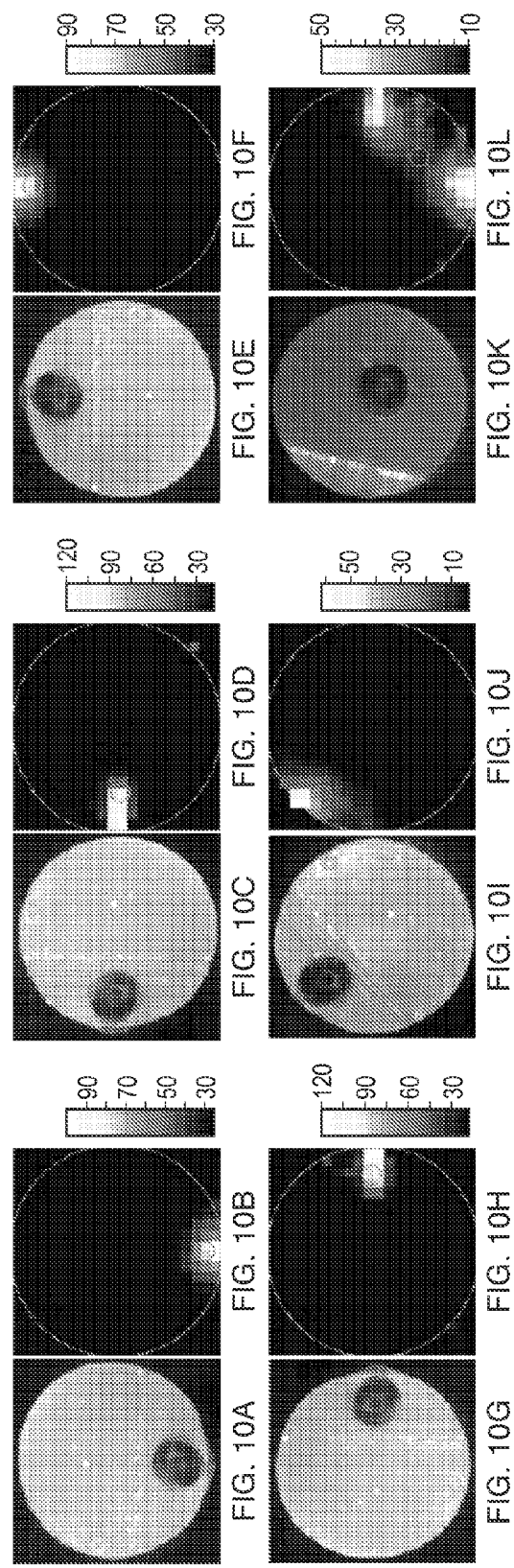

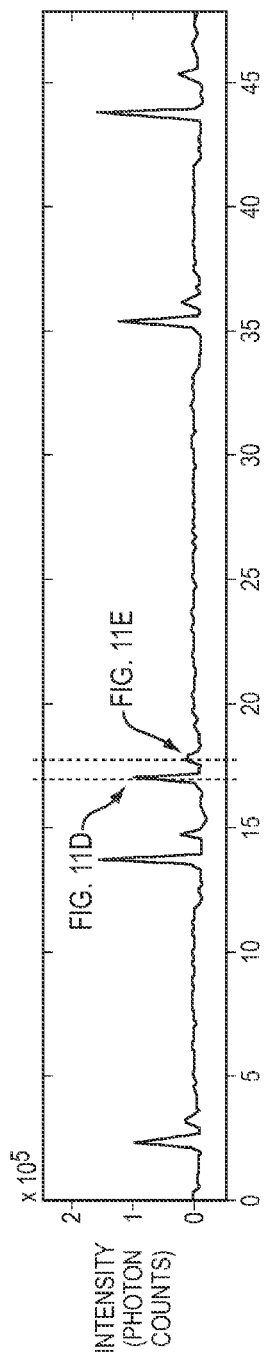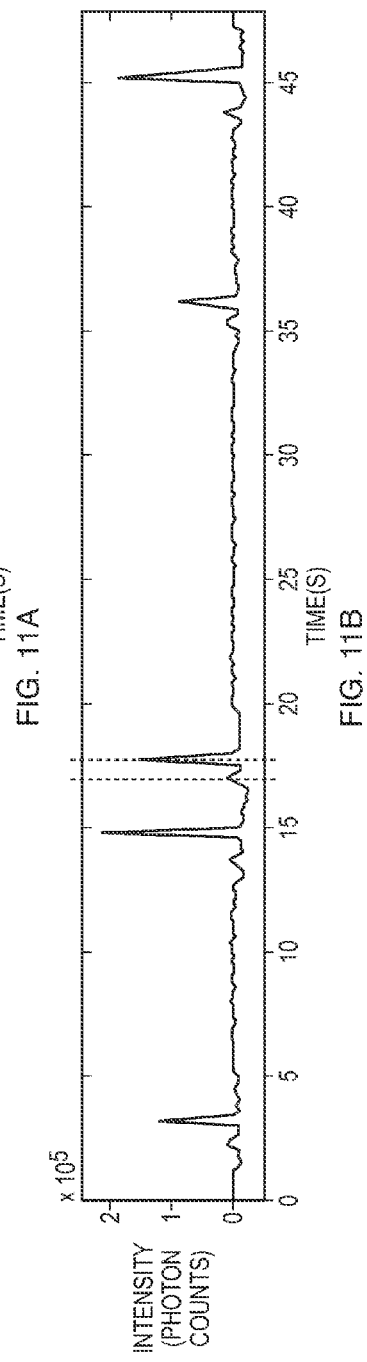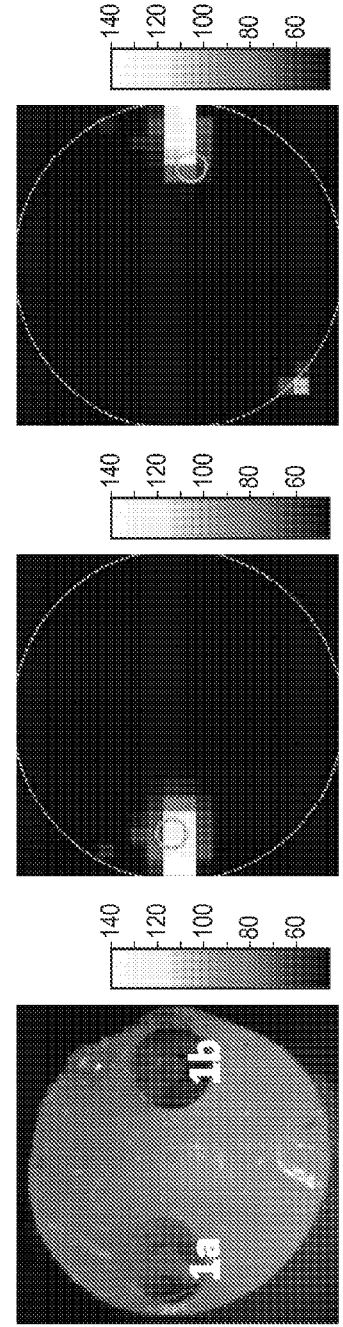
FIG. 11A
FIG. 11B
FIG. 11C
FIG. 11D
FIG. 11E

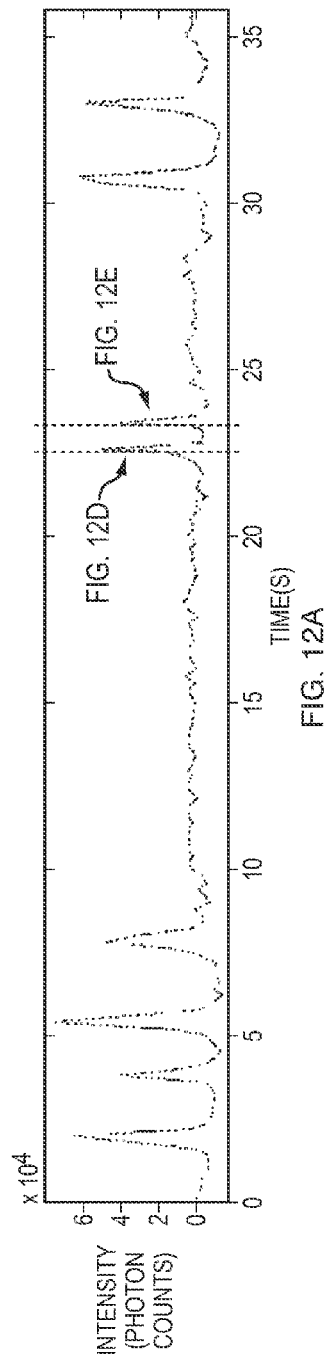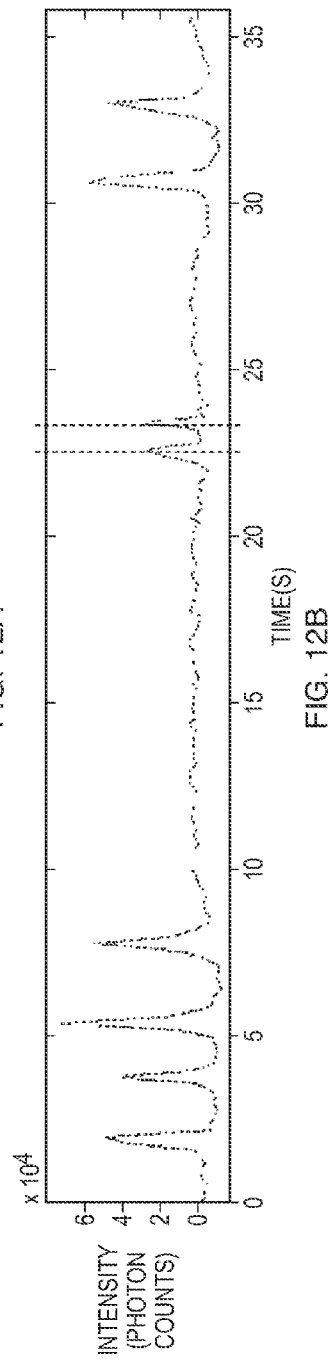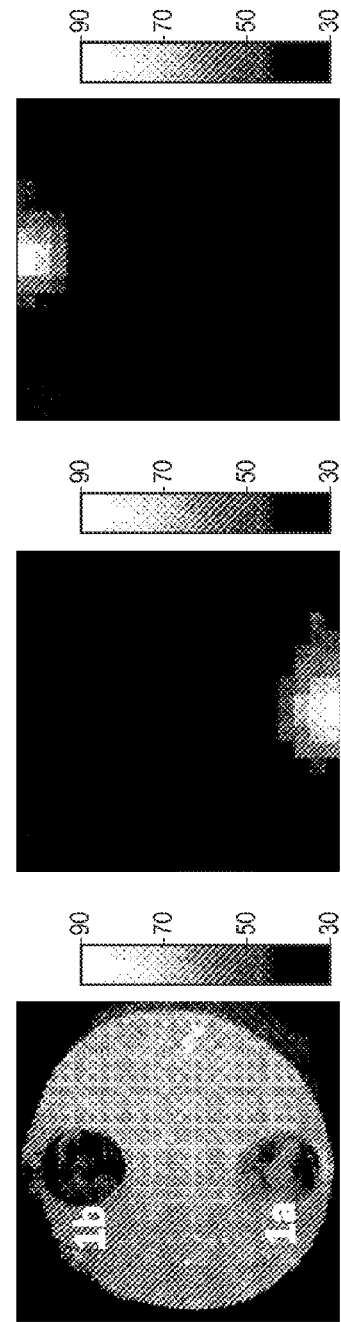

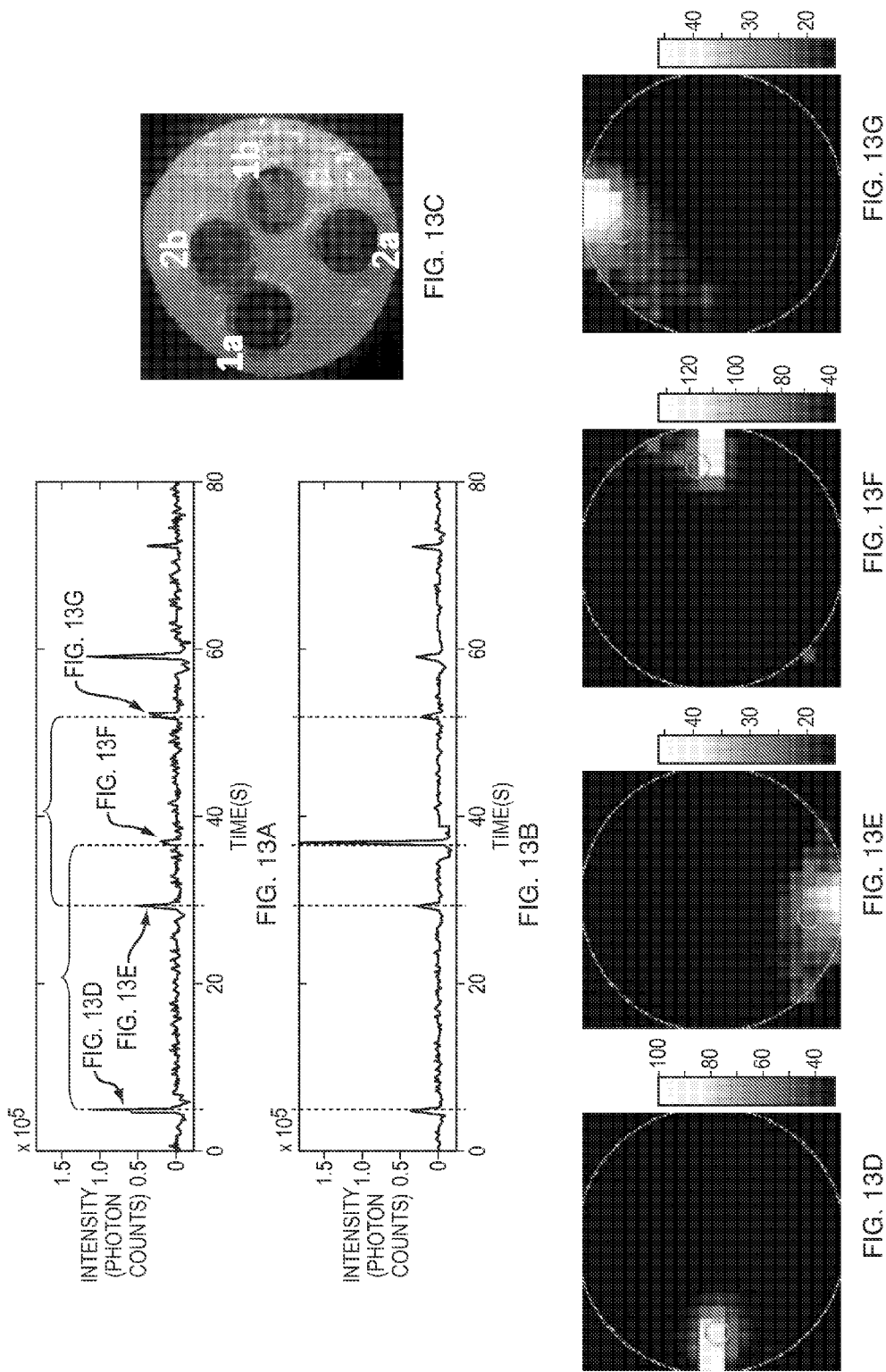

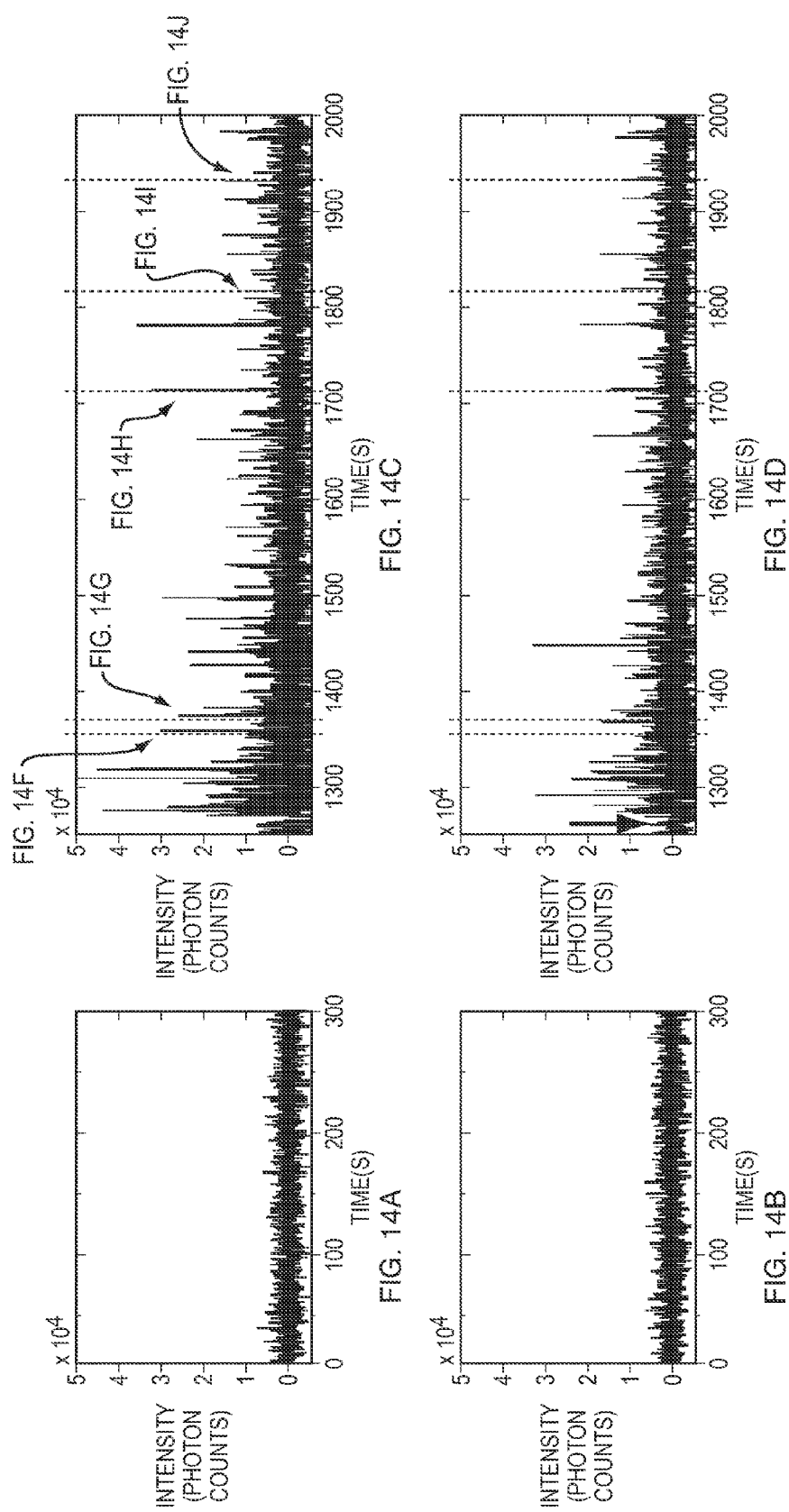

SYSTEMS AND METHODS FOR SENSING, ENUMERATING AND IMAGING RARE CELLS WITH DIFFUSE LIGHT

CROSS-REFERENCE TO RELATED APPLICATIONS

This application is the U.S. national stage application of International (PCT) Patent Application Serial No. PCT/US2013/022927, filed Jan. 24, 2013, which claims priority to U.S. Provisional Application No. 61/590,178 by Mark Niedre et al., filed on Jan. 24, 2012, the entire disclosure of each of which is hereby incorporated by reference for all purposes.

TECHNICAL FIELD

The invention relates to systems for imaging of living systems. More particularly, the invention relates to a system for imaging circulating cells using diffuse light.

BACKGROUND

The blood comprises a variety of different cells types. The most common cell type, the erythrocyte or red blood cell, which is responsible for carrying oxygen from the heart and lungs to the rest of the body, represents approximately 90% of the cells circulating in the blood and makes up approximately 45% of blood volume. Platelets, which are responsible for forming blood clots in response to injury, represent approximately 10% of the cells in the blood. Leukocytes, or white blood cells, generally comprise less than 0.5% of the cells in circulation, and subtypes of these cells (basophils, eosinophils, etc.) or other cells of interest, such as blood-borne bacteria or parasites, circulating stem cells, or mature leukocytes that are activated, transformed, cancerous, pre-cancerous, etc. are relatively rare, occurring at rates of fewer than one per ten-thousand cells.

Accurate quantification of these relatively rare cell populations is important in many areas of biomedicine. Cells in the blood are currently quantified either by extraction and analysis of small blood samples using, e.g., a hemocytometer, or using microscopy-based in vivo fluorescence flow cytometry. However, current approaches suffer from important limitations: first, their sensitivity is limited by the small number of cells that can be sampled using these methods; second, it is difficult to measure changes in cell populations over time; and third, extracted samples for quantitation can be cumbersome to handle, and can generate biohazardous waste.

SUMMARY OF THE INVENTION

Embodiments of the present invention overcome the limitations of currently used methods for quantitation of circulating cells using high-speed "diffuse fluorescence flow cytometry" for non-invasive in vivo detection of fluorescently labeled circulating cells that are present in amounts less than 1,000 cells/mL. The approaches described herein permit circulating cells to be assayed in relatively large limbs, thereby permitting a large fraction of the total circulating blood flow to be interrogated in a short period of time.

In one aspect, the invention relates to a diffuse fluorescence flow cytometer ("DFFC") that includes multiple excitation sources and detectors located circumferentially around a space for the limb of a subject, which limb includes circulating fluorophore-labeled cells. The DFFC also includes a processor that is responsive to both the excitation sources and the detectors, and which generates a tomographic reconstruction showing the location of fluorescence emitted within a cross-section of the limb. The detectors can be separated from one another by a fixed angular distance about the space, as can the excitation sources. The processor, in some embodiments, is configured to control the excitation sources according to executable instructions stored in a memory in non-transitory form, and the executable instructions, in turn, can include a timing waveform and a predetermined output intensity for the excitation sources (both depicted schematically in FIG. 8). In some embodiments, the DFFC includes multiple bandpass filters tuned to an emission peak of the fluorophore, which filters are located between the space and the detectors. In other embodiments, the DFFC includes a multi-channel photomultiplier tube, a preamplifier for amplifying the output of the photomultiplier tube, and multiple optical fibers connecting the detectors to the channels of the photomultiplier tube; the DFFC, in these embodiments, optionally includes a bandpass filter positioned between an optical fiber and a channel of the photomultiplier tube In another aspect, the invention relates to a method of determining the position of a fluorophore-labeled cell within the limb of a subject by surrounding the limb with multiple excitation sources and multiple detectors, operating the excitation sources to excite the fluorophore and operating the detectors to detect the fluorophore in the limb. Based on the detections of the fluorophore, a tomographic reconstruction is made showing the position of fluorescent emission within a cross-section of the limb. The reconstruction is optionally made in accordance with the following equation, in which b is a vector of measurements collected at each of multiple time points collected and W is a weighting function:

$$W \cdot x = b$$

The reconstruction thus generated is optionally compared with a cross-sectional image of the structure of the limb a correspondence between the fluorescent signal and a blood vessel is verified.

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "consists essentially of" means excluding other materials that contribute to function, unless otherwise defined herein. Nonetheless, such other materials may be present, collectively or individually, in trace amounts.

As used in this specification, the term "substantially" "about" or "approximately" means plus or minus 10% (e.g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

DRAWINGS

In the drawings, like reference characters refer to like features through the different views. The drawings are not necessarily to scale, with emphasis being placed on illustration of the principles of the invention.

FIGS. 3A-3F show intensity counts measured from each of six detection channels of a DFFC instrument during a 30 second interval in which a solution including labeled microspheres was flowed through an optical flow phantom.

Figure 4:
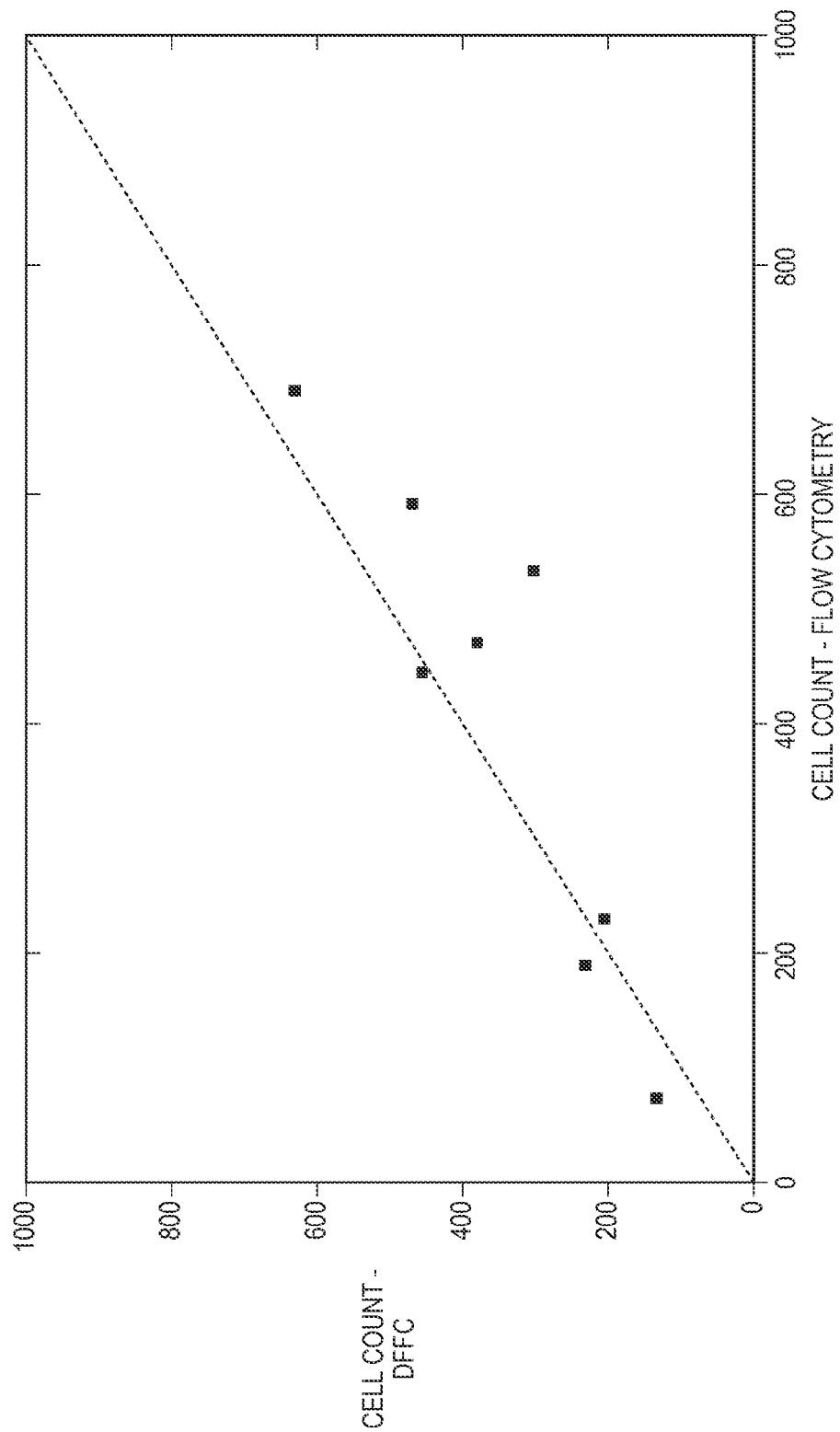

FIG. 4 plots the number of microspheres counted in the same 250 µL samples using a DFFC instrument (vertical axis) and a commercial flow cytometer (horizontal axis). The dashed line represents an idealized 1:1 correspondence between the DFFC and flow cytometer counts.

Figure 5:
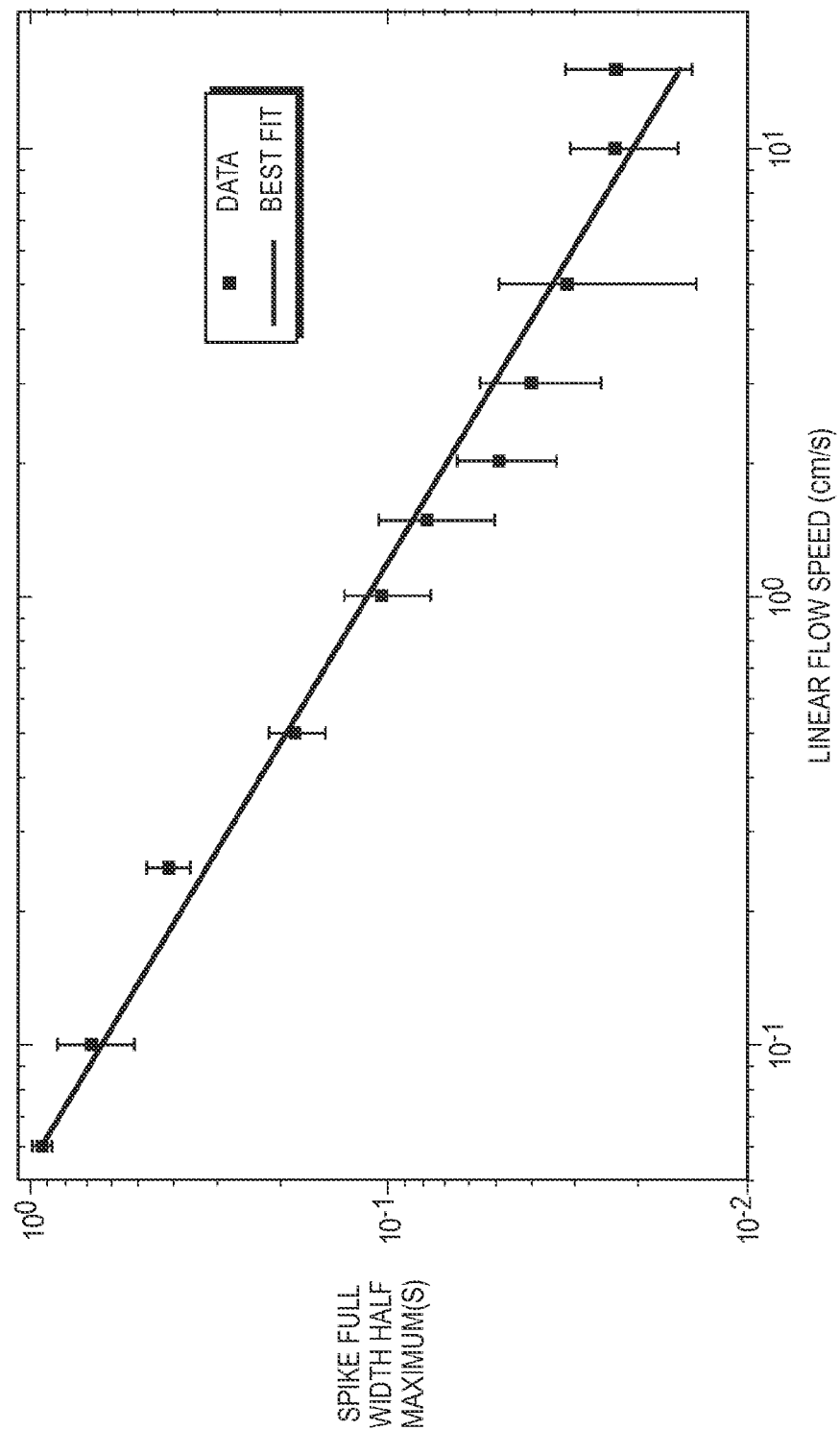
Figure 6A:
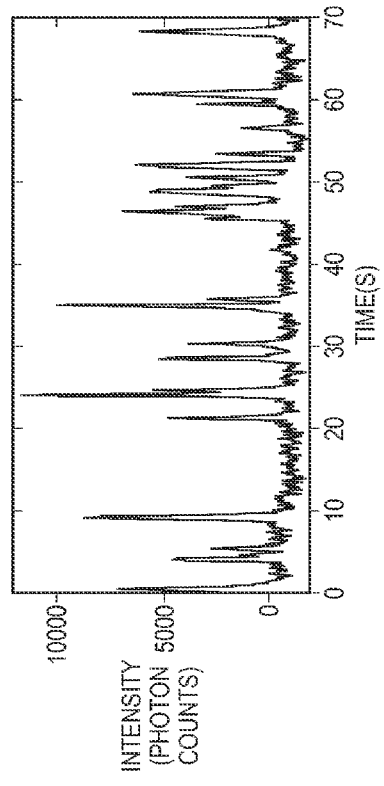
Figure 6B:
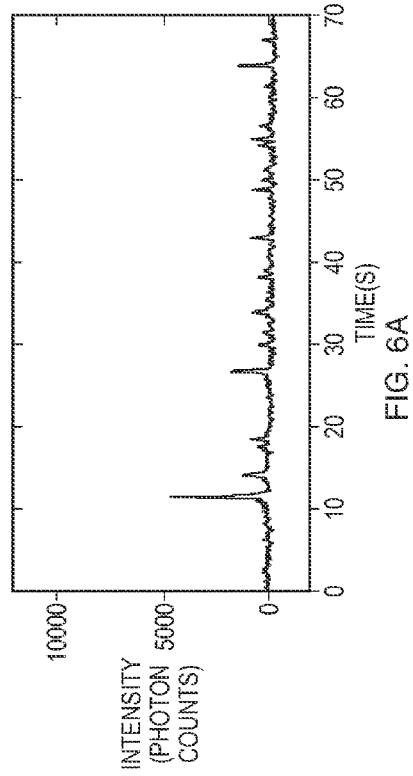
Figure 6C:
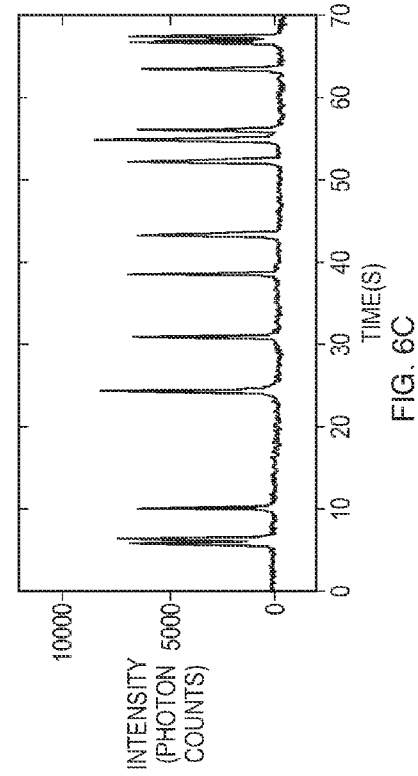
Figure 6D:
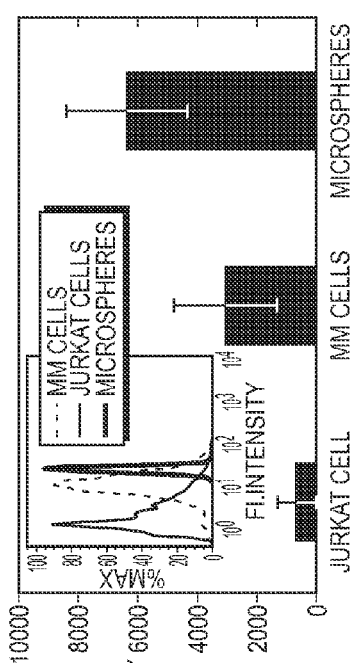

FIG. 5 is a table summarizing the relationship between spike width and linear flow speed.

FIGS. 6A-6D depict exemplary data from experiments in which live cells were passed through a flow phantom and detected using a DFFC instrument.

Figure 7A:
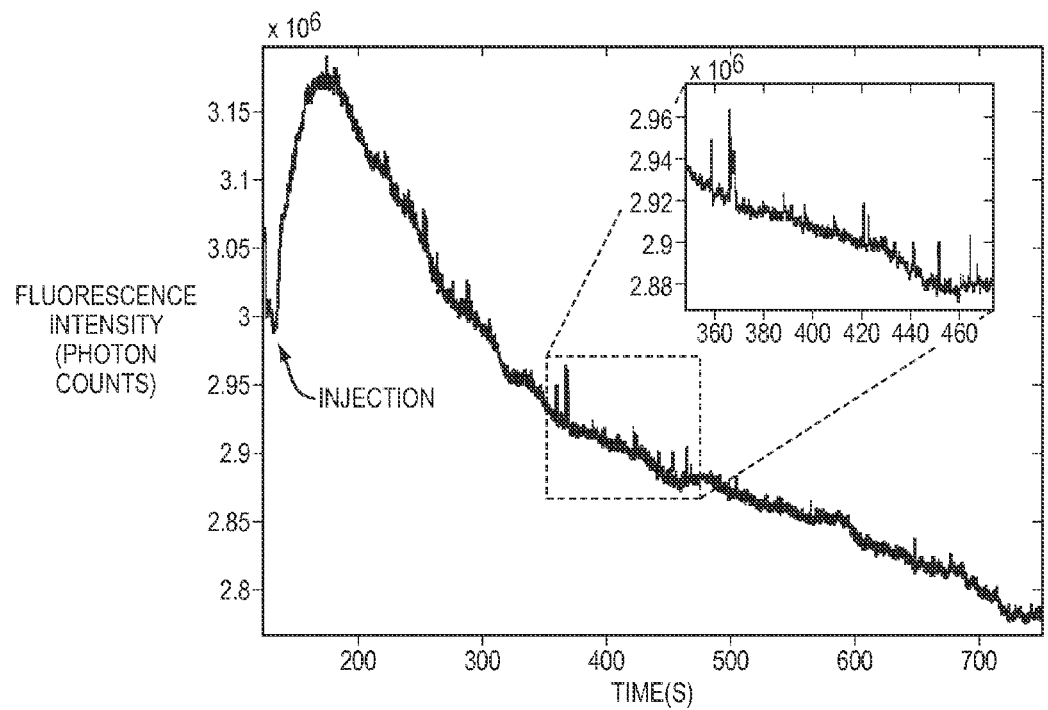
Figure 7B:
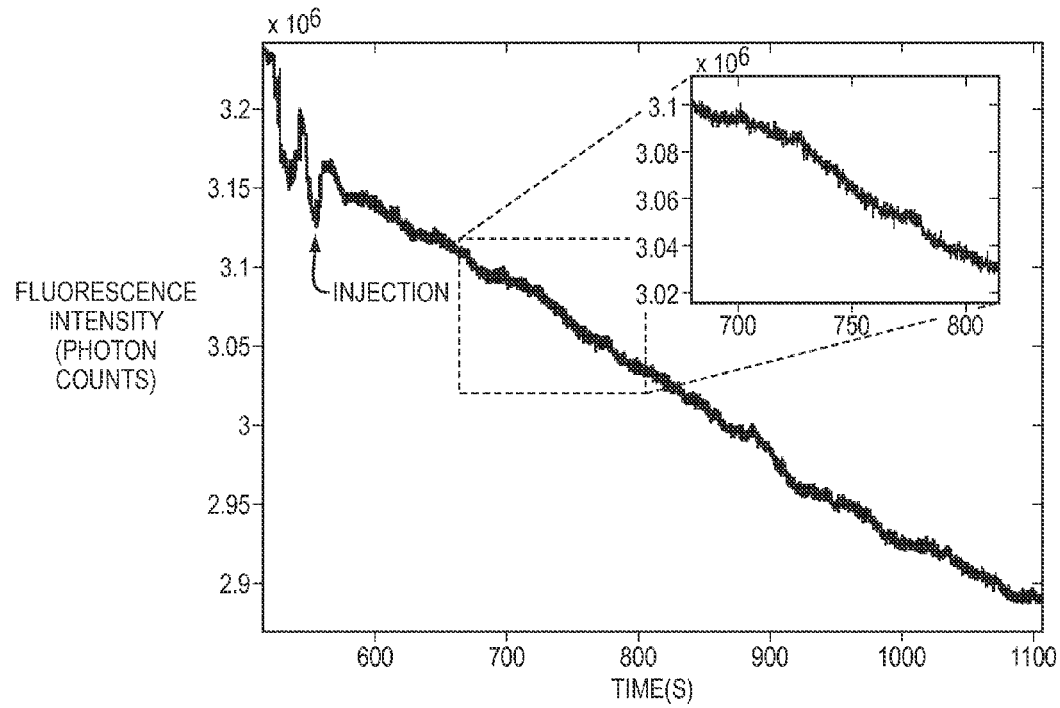

FIGS. 7A and 7B depict exemplary data from experiments in which live, VYBRANT DiD labeled multiple myeloma cells were injected retro-orbitally into live mice and were measured in the circulation of the tail using a DFFC instrument.

Figure 8:
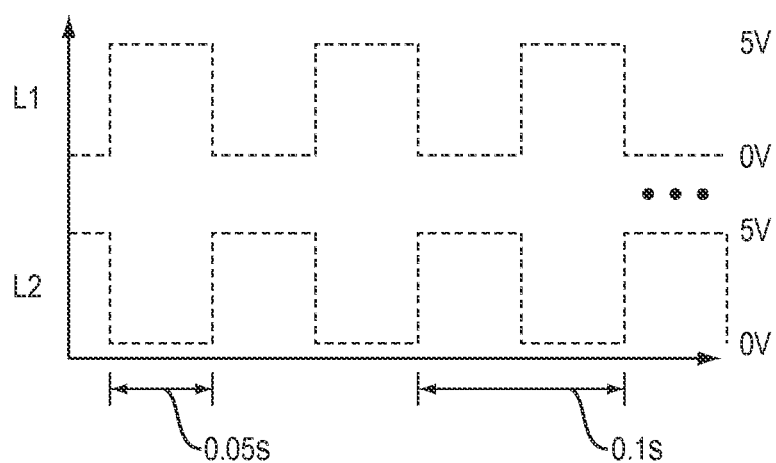

FIG. 8 depicts waveforms used to drive two laser excitation sources for tomographic reconstruction experiments.

Figure 9I:
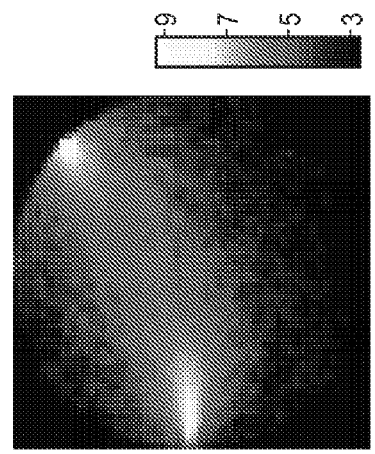
Figure 9H:
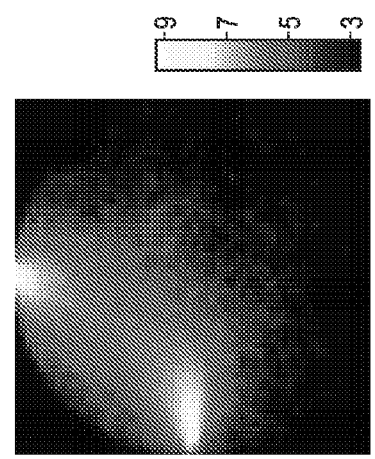
Figure 9G:
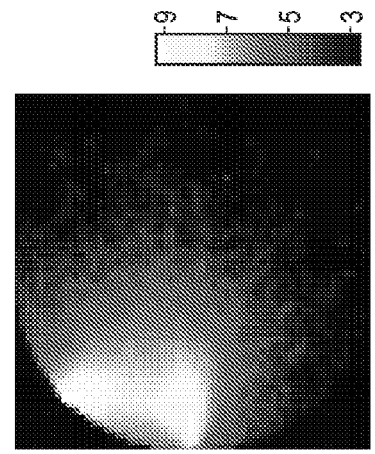

FIGS. 9A-9F depict exemplary photon counts from an initial tomographic reconstruction of a flow phantom using a DFFC instrument, while FIGS. 9G-9I depict exemplary weight functions between first and second lasers of an exemplary DFFC instrument.

FIGS. 10A-10L show tomographic reconstructions of single fluorescent microsphere spikes in single-tube flow phantoms and cross-sectional photos of the corresponding flow phantoms.

FIGS. 11A-11E illustrate single fluorescent microsphere spikes in double-tube flow phantoms as well as tomographic reconstructions of those spikes and cross-sectional photos of the corresponding flow phantoms.

FIGS. 12A-12E illustrate single fluorescent microsphere spikes in double-tube flow phantoms as well as tomographic reconstructions of those spikes and cross-sectional photos of the corresponding flow phantoms when rotated 90 degrees relative to the orientation of the phantoms in FIGS. 11A-11E.

FIGS. 13A-13G illustrate single fluorescent microsphere spikes in quadruple-tube flow phantoms as well as tomographic reconstructions of individual fluorescent spikes and a cross-sectional photo of the corresponding flow phantoms.

FIGS. 14A-14J illustrate single fluorescent microsphere spikes measured in vivo in the tail of a live mouse, well as tomographic reconstructions of individual fluorescent spikes and a cross-sectional photos of the tail indicating the positions of major blood vessels.

DETAILED DESCRIPTION

Figure 1:
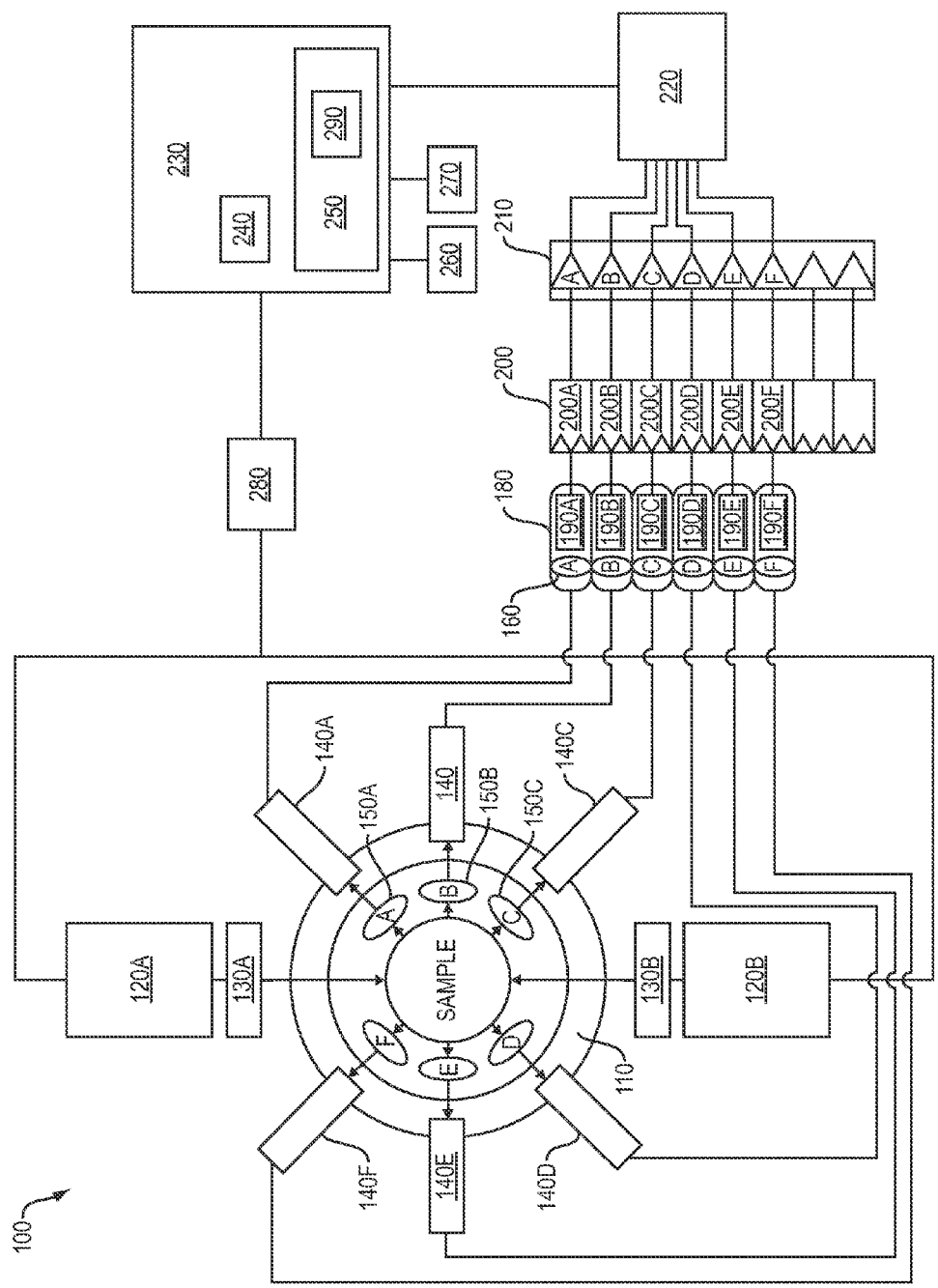
FIG. 1 is a schematic diagram of a DFFC instrument according to certain embodiments of the invention.

An exemplary diffuse fluorescence flow cytometer ("DFFC") 100 for quantitation of circulating cells is shown in FIG. 1. A ring assembly 110 sized to accommodate a limb of a subject in which circulating cells are to be quantitated includes a plurality (n) of excitation sources 120 separated by a suitable angular distance (such as 2π/n radians) about the ring assembly 110. Any excitation source 120 that generates sufficient power in a suitable band can be used in a DFFC instrument, including, without limitation, an arc lamp or a laser. FIG. 1 depicts a device having two excitation sources 120A, 120B, but any suitable number of excitation sources can be used, limited only by economic advantage and the ability to pack excitation sources 120 around one or more ring assemblies 110. Each excitation source 120A, 120B emits at one or more wavelengths selected to excite a fluorophore that is used to label cells of interest circulating within the subject. The output of excitation source 120A, 120B is optionally passed through a bandpass filter 130A, 130B to narrow the excitation band or bands to avoid overlap with any detection band or bands and to minimize background fluorescence.

Emitted fluorescence signals from the limb of the subject are collected by a plurality (m) of optical fibers 140 (also referred to as collecting fibers) arranged about the ring 110 as shown in FIG. 1. As with the excitation sources 120, each of the plurality of optical fibers 140 is separated from the other optical fibers 140 by an angular distance (such as 2π/m) to ensure capture of emitted fluorescence in substantially all directions The optical fibers 140 are optionally, but not necessarily, co planar and located within a single plane defined by the ring 100. In various alternate embodiments, however, the optical fibers are in different planes, or are angled to collect fluorescent emissions at various angles. For instance, in one alternate embodiment (not shown), multiple rings 110 are used to support a relatively large number of excitation sources 120 and fibers 140, which are fibers 140 angled to collect emitted fluorescence in a single plane located between the multiple rings 110 and excited by the excitation sources 120.

FIG. 1 depicts a device having six optical fibers 140A-140F but, again, any suitable number of collecting fibers can be used, limited only by economic considerations and the ability to pack the fibers around the ring assembly 110. To block diffusely and specularly reflected light from the excitation sources 120 from directly entering the optical fibers—and to thereby minimize non-specific background signals—bandpass filters 150, 160 tuned to an emission peak of the fluorophore can be positioned at either end, or at both ends, of the optical fibers 140. In the device depicted in FIG. 1, twelve bandpass filters 150A-150F and 160A-160F are used on each end of each optical fiber 140A-140F. At their far ends (relative to the limb of the subject), each optical fiber 140 terminates in a filter housing 180 comprising (or consisting of) bandpass filter 160 and a collimating lens 190. Again, in the device illustrated in FIG. 1, six filter housings 180A-180F, each comprising or consisting of a bandpass filter 160A-160F and a collimating lens 190A-190F, are positioned at the terminus of each optical fiber 140A-140F. The collimating lenses 190 direct the light collected by the optical fibers 190 to different anodes of multi-channel photomultiplier tube array (PMT) 200. The output from each channel of the PMT 200 generally requires amplification due to the small fluorescence signals from individual cells in the limb of the subject, so the output from each channel of the PMT 200 is amplified and optionally pre-processed—for example, to remove high-frequency noise using or low-pass filter, or to remove a DC signal component containing residual autofluorescence from the limb and autofluorescence—by a preamplifier 210 before being passed to a multi-channel scalar (MCS) photon-counting card 220 connected, directly or indirectly (via, for example, an analog-to-digital converter) to a computer 230. The computer 230, in turn, includes a processor 240, at least one volatile or non-volatile memory 250 and suitable inputs 260 and outputs 270. The volatile or non-volatile memory 250 optionally includes an analysis module 290 for constructing tomographic reconstructions and/or rejecting motion artifacts according to the methods outlined below; that is, the analysis module 290 includes instructions executable by the processor 240 in order to perform the necessary computations. More generally, the memory 250 may include procedural instructions according to which the processor controls the excitation sources 120; for example, the executable instructions may cause the processor to retrieve from memory a timing waveform and a predetermined output intensity, and to operate the excitation sources 120 in accordance therewith.

The computer 230—described in greater detail below—can be used passively (i.e., solely to collect data from the MSC photon counting card 220), or can optionally control one or more component parts of the DFFC 100. The DFFC can be manually controlled by a user or can be configured to operate partially or completely automatically, for example, through the use of a multi-function data acquisition card (DAQ) 280.

In operation, the DFFC 100 interrogates the circulation of a limb placed within the ring assembly 110 by illuminating the limb such that the light that reaches cells within blood vessels of the limb is a mixture of refracted and diffusely reflected light from the excitation source 120. Fluorescence emitted from fluorophore-labeled cells as they flow through blood vessels within the limb is collected by the optical fibers 140 disposed about the ring assembly 110, then fed through the multi-channel PMT 200, the preamplifier 210 and the MCS counting card 230. While the excitation sources 120 can be operated in any suitable way, methods of the invention include two principal modes of operation: first, at least one excitation source 120 can be continuously on during a period of measurement solely to allow the detection of fluorophore-labeled cells within the limb. Alternatively, a plurality (n) of excitation sources 120A, 120B separated, as discussed above, by an angular distance (e.g., $2\pi/n$) from one another are used to sequentially illuminate the limb: during a first interval, the first excitation source 120A illuminates the limb while the second excitation source 120B is off, and a first group of emission measurements are collected; then, during a second interval, the first excitation source 120A is off while the second excitation source 120B illuminates the limb and a second group of emission measurements are collected. This second mode permits the gross localization of fluorescent signals within the limb by generating, at each time point or sampling interval for which data is collected, a linear matrix according to the following Equation 1:

$$Wx=b \quad (1)$$

In Equation 1, b is the vector of measurements collected at each time point or sampling interval, W is a weighting function that can be calculated using the Boltzmann Transport equation or an approximation thereof or, in cases where the tissue volume being interrogated is small, using a Monte Carlo simulation of photon transport in diffusive media. The system defined by linear matrix x is solved using any suitable approach, including without limitation the singular value method or the randomized algebraic reconstruction technique (r-ART). Linear matrix x can be assumed to be sparse by adding the constraint that the emission come from a small target (such as a point) relative to the cross-section. This constraint limits the number of possible solutions of x, thereby improving the accuracy of the solution. Solving the system defined by x can also potentially be made simpler by assuming one or more of the following: (i) that the position of fluorescent cells does not move significantly during any single sampling interval; (ii) that the fluorescent signals arise from point sources; and (iii) that all fluorescent light that emerges at the surface of the limb is collected at an adjacent detector. In one exemplary implementation, for a system in which two light sources and six optical fibers are used, 12 measurements are taken during each sampling interval, which yields 12 equations and 144 unknown fluorescence concentrations.

Tomographic reconstructions made according to the methods described above are optionally compared with cross sectional images (obtained via direct dissection or structural tomographic methods such as CT scanning or MRI) of the region interrogated using the DFFC instrument to identify the positions of blood vessels. These cross-sectional images provide an indication of the quality of tomographic reconstructions according to the methods described above, and may be used to further refine any reconstructions, as the fluorescent signals preferably (though not necessarily) overlap with the locations of blood vessels.

DFFCs in accordance with the invention are preferably configured to emit in the red-to near-infrared region in order to maximize the penetration of photons into limb tissue, and therefore are preferably used to detect circulating cells labeled with fluorophores that have absorption peaks in this range, including without limitation VYBRANT DiD or a red fluorescent protein. Cells can be labeled in a variety of ways and for a variety of reasons. In one exemplary embodiment, a subject can receive exogenous cells that are labeled, either directly with a fluorophore, or indirectly, by introduction of a transgene encoding a fluorescent protein. In another example, a fluorophore-tagged molecule such as a receptor ligand or antibody can be injected into the subject so that circulating cells expressing, for instance, cell surface proteins complementary for the tagged molecule, are labeled and capable of being detected. Additional means of labeling cells will occur to those of skill in the art.

DFFC instruments are useful in a variety of commercial applications, including drug discovery, basic biomedical research and, for DFFC instruments configured to accommodate human limbs such as fingers, clinical research and the diagnosis and/or treatment of human disease. For example, a bone marrow graft administered to a patient may include a fraction of cells labeled as described above, and the viability of graft cells can be non-invasively assessed over time in the patient through periodic measurement of the frequency of labeled cells using a DFFC instrument. Alternatively, circulating cells in animal subjects can be repeatedly non-invasively assayed using a DFFC instrument.

DFFC instruments can advantageously be used to investigate conditions in which small numbers of circulating cells can give rise to fulminant disease. For example, DFFC instruments can be used to study minimal residual disease and/or in subjects by, for example, generating transgenic animals that express fluorescent proteins driven by one or more promoter regions for a cell-state marker of interest (e.g. a tumor-cell marker, a metastasis marker, a marker of a pre-cancerous state, etc.) Alternatively, transgenic animals that express fluorescent protein/tumor cell marker fusion proteins can be used. In either case, the presence or absence of fluorescent cells can be repeatedly non-invasively assayed at different times, in response to different experimental conditions, etc. using a DFFC instrument according to the invention.

In order to minimize artifacts arising from movement of the limb during measurements, the limb is optionally secured, for example by taping, during the period of measurement. Alternatively, or in addition, a motion-artifact rejection algorithm can be applied to datasets to remove motion artifacts that might otherwise obscure or be mistaken for fluorescent signals emitted from labeled cells. A DFFC instrument 100 according to the invention can be modified to add a detection channel (for example, comprising one or more of an optical fiber 140G, bandpass filter(s) 150G, 160G, collimating lens assembly 180G comprising a collimating lens 190G, which feed into an unused channel of a PMT 200 and, again optionally, preamplifier 210 as may be used in the DFFC instrument 100). The additional detection channel is tube tuned to detect "out of band" fluorescence that does not correspond to fluorescence emissions from labeled cells, but instead consists of background autofluorescence that varies with subject motion in a manner substantially similar to the "in-band" signal. A motion-artifact-corrected trace is generated in accordance with Equation 2:

$$I_{corrected}(t) = I_{in\text{-}band}(t) - \alpha \cdot I_{out\text{-}of\text{-}band}(t) \quad (2)$$

In Equation 2, the corrected trace $I_{corrected}(t)$ is generated by subtracting an out-of-band trace $I_{out\text{-}of\text{-}band}(t)$ that has been scaled by a scaling factor $\alpha$ from the in-band trance $I_{in\text{-}band}(t)$. The scaling factor $\alpha$ reflects the relative intensity difference between the in-band and out-of-band fluorescence channels, and estimating this scaling factor accurately is critical to the success of motion-artifact correction. In some embodiments, the scaling factor can be estimated simply by comparing the mean value of the in-band and out-of-band traces in a control subject that does not contain any labeled cells. However, the mean signal can vary substantially among different subjects, so this approach may not be robust for all fluorophores or all subjects. A more robust approach may involve comparing, for each subject, the relative variances of the in-band and out-of-band traces, according to Equation 3:

$$\alpha = \sigma^2_{in\text{-}band} / \sigma^2_{out\text{-}of\text{-}band} \quad (3)$$

Assuming that some points within the in-band trace correspond to labeled cells, the accuracy of an estimate of the scaling factor $\alpha$ can be improved by excluding points in the in-band trace (and optionally the out-of-band trace) from the calculation of the scaling factor $\alpha$. In various embodiments, a percentage of points exhibiting the greatest deviation from the mean of the trace is excluded. The specific percentage will preferably be determined empirically, but can be, for example, 1%, 5%, 10%, 20%, 25%, 30%, etc.

The DFFC instrument 100 includes a ring assembly 110 sized to permit insertion of a limb of a subject. In preferred embodiments, the ring assembly has an inner diameter of approximately 5 mm (e.g., 1 mm, 2 mm, 3 mm, 4 mm, 5 mm, 6 mm, 7 mm, 8 mm, 9 mm 10 mm, 12 mm or more), but any suitable inner diameter can be used. It currently appears that satisfactory tissue penetration and resolution of fluorescent spikes can be achieved in limbs up to about 20 mm in diameter, such as human fingers, earlobes or toes. Additional penetration may be achieved using multiple ring assemblies 110 comprising relatively larger numbers of detectors 140 and excitation sources 120, and such arrangements are within the scope of the invention.

As noted above, the computer 230 includes a processor, at least one volatile or non-volatile memory 250 and suitable inputs 260 and outputs 270. More generally, the computer 230 may be or include a general-purpose computing device including a system bus that couples various system components, including the system memory, to the processor. Computers typically include a variety of computer-readable media that can form part of the system memory and be read by the processing unit. By way of example, and not limitation, computer readable media may comprise computer storage media and communication media. The system memory may include computer storage media in the form of volatile and/or nonvolatile memory such as read only memory (ROM) and random access memory (RAM). A basic input/output system (BIOS), containing the basic routines that help to transfer information between elements, such as during start-up, is typically stored in ROM. RAM typically contains data and/or program modules that are immediately accessible to and/or presently being operated on by processing unit. The data or program modules may include an operating system, application programs, other program modules, and program data. The operating system may be or include a variety of operating systems such as Microsoft WINDOWS operating system, the Unix operating system, the Linux operating system, the Xenix operating system, the IBM AIX operating system, the Hewlett Packard UX operating system, the Novell NETWARE operating system, the Sun Microsystems SOLARIS operating system, the OS/2 operating system, the BeOS operating system, the MACINTOSH operating system, the APACHE operating system, an OPENSTEP operating system or another operating system of platform.

The computing environment may also include other removable/nonremovable, volatile/nonvolatile computer storage media. For example, a hard disk drive may read or write to nonremovable, nonvolatile magnetic media. A magnetic disk drive may read from or writes to a removable, nonvolatile magnetic disk, and an optical disk drive may read from or write to a removable, nonvolatile optical disk such as a CD-ROM or other optical media. Other removable/nonremovable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The storage media are typically connected to the system bus through a removable or non-removable memory interface.

The methods and techniques describe above may be implemented in hardware and/or software and realized as a system for non-invasive in vivo detection of fluorescently labeled circulating cells. The system may also use one or more processors and/or use portions of a computer's random access memory to provide control logic that implements collection and analysis of emission measurements (including control of the excitation sources and solution of Equation 1 based on the data). In such an embodiment, the program may be written in any one of a number of high-level languages, such as FORTRAN, PASCAL, C, C++, C#, Java, Tcl, or BASIC. Further, the program can be written in a script, macro, or functionality embedded in commercially available software, such as EXCEL, MATLAB or VISUAL BASIC. Additionally, the software could be implemented in an assembly language directed to a microprocessor resident on a computer. For example, the software can be implemented in Intel 80×86 assembly language if it is configured to run on an IBM PC or PC clone. The software may be embedded on an article of manufacture including, but not limited to, computer-readable program means such as a floppy disk, a hard disk, an optical disk, a magnetic tape, a PROM, an EPROM, or CD-ROM.

DFFC instruments according to the various embodiments discussed herein have significantly improved sensitivity relative to currently-used systems and methods currently used in the art. Currently used hemocytometry protocols permit detection of cells down to a limit of approximately 100 cells per mL. Similarly, currently used in vivo flow cytometers sample approximately 1-5 µL of blood per minute (of the ~2.5 mL of blood in the circulatory system of a mouse), implying a detection limit of $10^3$-$10^4$ cells/mL, for each ~30 minute sampling window. By contrast, the total blood volume fluxing through the tail of a mouse is between 0.2 and 0.5 mL per minute, meaning that the entire circulation of a mouse can be interrogated using a DFFC instrument in 5-10 minutes, and by extension that the DFFC instrument has a theoretical detection limit of a single cell within the circulatory system of the mouse, and can detect fewer than 1 cell/mL in relatively short sampling windows.

The principles of the invention and its various aspects are further illustrated by the following examples:

Example 1: The DFFC Instrument

A DFFC instrument as depicted in FIG. 1 was made and its ability to identify fluorescent signals emitted from point sources tested. The sample—either a synthetic, limb-mimicking flow phantom, discussed in greater detail below, or the limb (leg or tail) of a live mouse—was placed in the center of the ring assembly 110 and was illuminated by one of two solid state lasers 120A, 120B emitting at 642 nm (DL640-050-O, CrystaLaser Inc., Reno, Nev.). The output of each laser was passed through 640 nm excitation 'cleanup' filters 130A, 130B with a 10 nm bandpass (Z640/10x, Chroma Technology, Rockingham, Vt.) and the power at the sample was 15 mW with a spot size of 1 mm diameter. For the work described in the following Examples 2-6, a single laser was operated in continuous wave (CW) mode.

Emitted fluorescence signals from the sample were detected with six optical fibers 140 that were arranged at regular intervals around the ring assembly 110. Specially cut 2×3 mm filters 150 centered at 700 nm with a 50 nm bandpass (ET700/50, Chroma Technology, Rockingham, Vt.) were placed in front of collection fibers 140; the filters blocked diffusely and specularly reflected light from directly entering the fiber and generating secondary autofluorescence. On the opposite end the fibers 140 were terminated on a custom designed filter housing 180 with collimating lenses 190 and a second, 700 nm filter 170 (Chroma) placed in front of each anode of an 8-channel photomultiplier tube array 200 (PMT; H9530-01, Hamamatsu Photonics, Japan). The use of two filters 150, 160 for each detector fiber 140 was empirically determined to be necessary since the emitted fluorescence from individual cells was very small and even modest amounts of autofluorescence or laser light leakage could obscure the signal. The output from each channel of the PMT 200 was then amplified with a 1.6 GHz 8-channel preamplifier 210 with 26 dB gain (HFAM-26 dB-10, Boston Electronics, Boston, Mass.) and passed into a 8-channel multi-channel scalar (MCS) photon counting card 220 (PMM-328, Boston Electronics) installed in a personal computer 230 (NIXSYS Open Systems, Santa Ana, Calif.). This instrument design allowed high-sensitivity photon counting from each of the six detection optical fibers 140 simultaneously (the two additional PMT channels were unused). The photon counting threshold was set to −100 mV for each channel and the sampling rate was set to a rate of 100 samples/sec. The maximum number of photon counts per time sample was 65,535 counts (hardware limited) on each of the 6 detection channels. For each experiment the MCS card was configured to continuously acquire for 7500 samples, which was equivalent to 75 seconds. The 75-second measurement 'run' could be repeated an arbitrary number of times with approximately a 0.1 second time delay between cycles to allow for writing of the data to the hard drive. Experimental automation was performed using the analog outputs of a multi-function data acquisition card (DAQ; NI-USB-6251, National Instruments, Austin, Tex.) controlled with the same personal computer.

Example 2: Limb-Mimicking Optical Flow Phantom

To characterize the DFFC instrument 100, optical flow phantoms 300 were developed that were similar in size, optical properties and flow speeds to a mouse limb or tail. The phantoms 300 were constructed from polyester resin material (Casting Craft, Fields Landing, Calif.) with Titanium Oxide ($TiO_2$; Sigma-Aldrich Inc., St. Louis, Mo.) and India ink (Higgins Ink, Bellwood, Ill.) added to adjust the optical properties. Phantoms 300 were first made with final optical properties close to that of biological tissue at near-infrared wavelengths, specifically with reduced scattering coefficient $\mu'_s$=15 cm$^{-1}$ and absorption coefficient $\mu_a$=0.1 cm$^{-1}$. (These baseline optical properties were used for all experiments described herein unless otherwise specified.) The liquid resin material was placed in a 3 mm diameter×1 cm cylindrical mold with a length of 250 µm internal diameter TYGON tubing 310 (TGY-010-C, Small Parts, Inc., Seattle, Wash.) passed through the center before hardening. During phantom characterization experiments the TYGON tubing 310 was connected to a 30-gauge insulin syringe 320 (Easy Touch, Loveland, Ohio) that contained a solution of either fluorescent microspheres or fluorescently-labeled cells as described below. The syringe was placed in a microsyringe pump 330 (70-2209, Harvard Apparatus, Holliston, Mass.) that could be configured to produce linear flow rates in the range of 600 µm/sec to 15 cm/sec.

Figure 2:
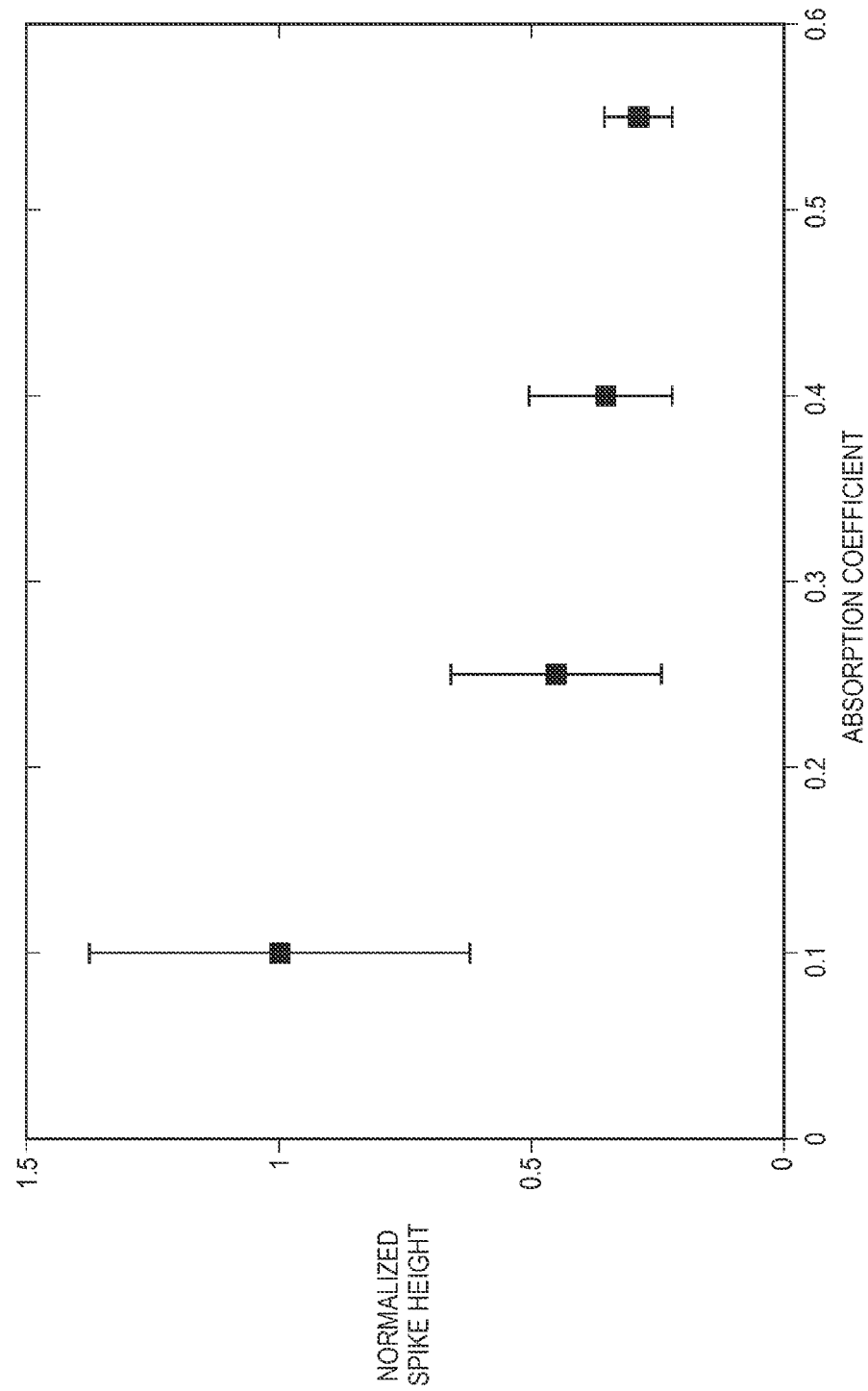
FIG. 2 is a graph summarizing normalized spike heights measured in flow phantoms having varying absorption coefficients.

To investigate the effect of the flow phantom optical attenuation on the measured fluorescence signal, a set of phantoms 300 was constructing using increasing concentrations of India Ink. The final absorption coefficients of the phantoms were; $\mu_a$=0.1, 0.25, 0.4 and 0.55 cm$^{-1}$. Measurements were repeated four times for each ink concentration. These data are summarized in FIG. 2. Unsurprisingly, increasing the absorption coefficient reduced the amplitude of measured spikes; specifically, increasing $\mu_a$ by a factor of 5.5 decreased the amplitude of the measured spikes by a factor of 4. However in all cases, microspheres were easily detectable above the background. This range of absorption coefficient covers reported literature values in the red and near-infrared region for biological tissues and therefore shows the feasibility of this technique in a phantom model. Further, we added ink to the PBS media in which the microspheres were suspended so that $\mu_a$ of the media was increased from 0 to 0.6 cm$^{-1}$. Increasing the absorption coefficient here had negligible effect on the measured spike height in this range (data not shown) since the volume of PBS in the 250 µm diameter tubing was very small compared to the bulk phantom material.

To test the tomographic imaging capabilities of the DFFC instrument, optical flow phantoms were developed with increasing complexity of 1, 2 or 4 lengths of TYGON tubing embedded therewithin to simulate the presence of multiple blood vessels in a mouse limb. For "single-tube" flow phantoms, a length of tubing was passed either close to the edge of the phantom to simulate a superficial blood vessel, or close to the center to simulate a deeper seated blood vessel (N=4 for each). "Double-tube" flow phantoms were made by embedding a single length of tubing that was passed along one edge of the phantom, then looped approximately 1 cm from the end and passed back through the resin a second time before hardening. As such, each microsphere would pass through the DFFC field of view twice on the return trip through the phantom. Finally, "quadruple-tube" phantoms were made in which two separate strands of TYGON tubing were passed through the phantom twice each in a loop, thereby creating 4 separate flow channels to mimic the four major blood vessels in the tail of a mouse.

Example 3: Characterization of DFFC Sensitivity

To assess the counting accuracy of the DFFC instrument 100, microspheres were suspended in PBS and 250 µL samples were passed through a flow phantom 300 at a constant linear flow speed of 1 cm/s. A total of 8 samples in the range of less than 10$^3$ microspheres/mL were prepared. Accurate dilution of microsphere solutions at very low concentrations is difficult; therefore, to obtain "true" microsphere concentrations the samples were collected in a microcentrifuge tube after analysis. Collected samples were subsequently counted with a commercial flow cytometer (Cell Lab Quanta S.C., 771917, Beckman Coulter, Brea, Calif.), which has ±5% accuracy in the range of 3×10$^4$ to 2×10$^6$ spheres/mL.

To obtain a total microsphere count with the DFFC instrument 100, a thresholding algorithm was applied to the measured data. When a fluorescent microsphere passed through the instrument detection ring a transient fluorescence signal (i.e., a "spike") was recorded. The signals from all six detection channels were summed and any fluorescence spike exceeding one standard deviation above the maximum measured background—determined by first running a blank sample of PBS through the flow phantom—was counted as a single microsphere. In practice, this threshold was approximately 300 photon counts. The count total for the 250 µL sample was then multiplied by four to arrive at a concentration in microspheres per mL for direct comparison to the commercial flow cytometer measurements. No adjustments were made to account for possible simultaneous arrival of more than one microsphere (i.e., "double spikes"), though such adjustments are within the scope of the invention.

FIG. 3 shows an example data set collected from each of the 6 detection channels of the DFFC instrument 100 over a 30 sec interval when fluorescent microspheres were run through a limb-mimicking optical flow phantom 300. For this experiment, a concentration of 500 microspheres/mL with a flow speed of 1 cm/s was used. As each fluorescent microsphere passed through the instrument field of view, a transient fluorescent signal (a "spike") was observed; spikes are demarcated in the first channel graph of FIG. 3 with arrows. As shown, the amplitudes of these spikes were typically in the range of 1000 to 5000 photon counts above the background, depending on the detection channel. Intra-spike variability in amplitude and width was observed even within a single detection channel. This was primarily due to variations in speed across the flow profile inside the TYGON tubing, because microspheres near the center of the tubing move at a faster rate than near the walls of the tubing. This was confirmed by observing the movement of fluorescent microspheres in bare TYGON tubing with a fluorescence microscope. For analysis of signals when a single laser is operated in continuous wave mode (i.e., for analyses that do not require localization of signals), the signal from all 6 channels can be summed. Alternatively, each channel can be treated independently, especially to approximately localize the site of emission (the cell) in the cross-section of the sample.

The detection sensitivity of the DFFC instrument was investigated further using flow phantoms. Using the thresholding algorithm described above, a DFFC instrument and a commercial flow cytometer were both used to count the number of microspheres in the same 250 µL samples and the counts obtained by each method were compared. FIG. 4 shows a cell count comparison between microspheres on the DFFC instrument and the flow cytometer for a set of 8 experiments, all of which were in the target concentration range of less than 10$^3$ cells per mL. The dashed line indicates the ideal 1-1 correspondence between the two systems. Generally, very good correlation between the two instruments was observed, with a mean error of less than 20%. Note that the microsphere concentrations used here were at least an order of magnitude below the recommended operating range of the commercial flow cytometer of 3×10$^4$ cells/mL. Therefore, deviations between the two measurements are at least partly due to the accuracy of the commercial system at low concentrations (as opposed to the DFFC prototype). Nevertheless, it is clear that the DFFC instrument detects individual fluorophore-labeled bodies with very high sensitivity.

Example 4: Characterization of Useful DFFC Flow Speed Ranges

Since a range of blood flow rates are likely to be present in the instrument field-of-view in a mouse limb in vivo (due, for example, to the presence of different-size blood vessels within the limb being interrogated), experiments were conducted to determine the range of flow speeds at which a DFFC system 100 could detect single microspheres. Microsphere suspensions were prepared in the range of 10$^2$ to 10$^3$ spheres/mL. 1 mL samples were then run through the flow phantom 300 at varying linear flow speeds between 600 µm/sec and 15 cm/sec. The latter value reflects a higher flow speed than would be expected in limb blood vessels in mice in vivo, while the former value is the lowest flow speed that the microsyringe pump could produce, and not necessarily a detection limit of the DFFC instrument. Experiments were repeated three times for each flow speed. As above, the signals from all six channels were summed and measured fluorescent "spikes" were analyzed to obtain the full width half maximum (FWHM)—defined as the duration of time between data points with magnitude halfway between the maximum value for a given spike and the mean background—for each. All spikes were analyzed for each experimental condition and the mean and standard deviation FWHM was recorded.

These data are summarized in FIG. 5. Each data point represents the mean and standard deviation of at least 100 fluorescent spikes at each flow speed. Note that the relatively large standard deviations for each point shown do not reflect "error" in the measurements, but real observed variations in flow speeds of the microspheres across the flow profile as discussed above. Finally, it is interesting to note that the linearity of the curve plotted on a log-log scale is consistent with the anticipated "1/x" relationship, since the product of each FWHM and flow speed combination must equal the fixed instrument field-of-view. This analysis also permits an estimate of the field-of-view of the DFFC instrument, which in this instance is approximately 0.7 mm.

Example 5: Characterization of Fluorescently-Labeled Cells

The ability of the DFFC instrument to detect fluorescently labeled cells in flow phantoms was tested using either Jurkat T-Lymphocyte cells (American Type Culture Collection, Manassas, Va.) or Multiple Myeloma (MM) cells (Northwestern University, Chicago Ill.). Jurkat T-Lymphocytes were cultured in 75 cm$^2$ tissue culture flasks at 37° C. in a humidified atmosphere with 5% $CO_2$ and 95% air. The cells were cultured in RPMI 1640 supplemented with 100 U/mL penicillin, 100 µg/mL streptomycin and 10% fetal bovine serum (FBS). Cells were grown to confluence (approximately 1×10$^6$ cells/mL) and then dyed with 10 µmol/L of VYBRANT DiD (V-22887, Invitrogen) cell labeling solution incubated for 30 minutes. VYBRANT-DiD is a non-specific lipophilic dye that brightly labels cell membranes without loss of viability. The cell suspension was centrifuged and washed repeatedly in PBS, and then resuspended in PBS at final concentrations of approximately 10$^3$ cells/mL.

Multiple Myeloma cells were harvested using Trypsin and spun down at 400g and then resuspended in RPMI with 0.1% Bovine Serum Albumin (BSA) at a concentration of 1×10$^6$ cells/mL. Cells were dyed using a final concentration of 1 µmol/L of VYBRANT-DiD and incubated for 30 minutes at 37° C. At the end of the incubation process, FBS was added (2% of total volume) to prevent cell clumping during centrifuging. Cells were centrifuged as before and washed, once with RPMI with FBS to remove any free DiD in suspension, and again with RPMI only. They were then resuspended at approximately 10$^3$ cells/mL.

The syringe pump was configured to produce a linear flow speed of 1 cm/sec. Following data collection, the signal from each of the six detection channels was summed and the fluorescence spike amplitude from each cell was analyzed to determine the relative fluorescence intensity compared to fluorescent microspheres. The fluorescence signal from the cells and microspheres were also quantified with the commercial flow cytometer for comparison with the DFFC instrument.

Example data—summed from all 6 detection channels—is shown in FIG. 6. Example data from VYBRANT-DiD-labeled Jurkat cells (FIG. 6a), MM cells (FIG. 6b) as well as data measured from fluorescent microspheres (FIG. 6c) are shown for comparison. The relative mean and standard deviation of measured fluorescent spike heights for each case is shown in FIG. 6d, averaged over at least 1000 individual spikes. From these data, it can be seen that the microspheres had the highest fluorescence intensity on average, followed by the MM cells and the Jurkat cells which exhibited about 48% and 10% of the fluorescence intensity of the microspheres, respectively. These relative intensities also generally agreed well with "conventional" flow cytometry analysis (FIG. 6d inset), which showed that MM cells were on average about 50% as bright as fluorescent microspheres, and Jurkat cells were approximately 6% as bright as microspheres. Although fluorescently-labeled cells exhibited lower emitted fluorescence than the fluorescent microspheres, the DFFC instrument robustly detects diffuse fluorescent light from individual cells passing through an optical flow phantom.

Example 6: Experiments in Mice In Vivo

As an initial in vivo test of the DFFC instrument, a limited number of experiments were performed in mice using injected Multiple Myeloma (MM) cells. All mice were handled in accordance with Northeastern University's Division of Laboratory Animal Medicine policies on animal care. MM cells were used since they have been used previously for microscopy based in vivo flow cytometry experiments and circulate with known kinetics. Further, MM cells exhibited better VYBRANT-DiD labeling (measured intensity) than Jurkat cells. Nude (nu/nu) mice first were anesthetized using a cocktail of Ketamine (100 mg/kg) and Xylazine (5 mg/kg) injected i.p. Mice were then placed on an adjustable platform with a warming pad and the tail was passed through the detection ring. The tail was gently secured at each end with medical tape so that it would remain taut (but not tight enough to restrict circulation) in order to minimize breathing movement artifacts.

A total of 10$^6$ VYBRANT-DiD labeled MM cells were suspended in 100 µL in RPMI. Cells were injected retro-orbitally into the mice (N=3) while the instrument was operating so that changes in the measured fluorescence signal could be observed immediately after the injection. Measurements were made until approximately 15 minutes after injection. Control (sham) injections were also performed using unlabeled MM cells on a separate set of mice (N=3).

Results of the preliminary in vivo testing of our DFFC instrument in mice are shown FIG. 7. Example data for mice injected with fluorescently-labeled MM cells and unlabeled control cells are shown in FIGS. 7a and 7b, respectively. Note here that the time-scale is approximately 15 minutes for both experiments (i.e., significantly longer than in previous figures), and the data from multiple time bins has been summed to 0.1 sec increments. Magnified (120 sec) portions of the curves are shown in the inset figures. The arrows indicate the time of the retro-orbital injection; signal fluctuations immediately prior to the injections were caused by unavoidable movement of the mouse during the injection. When fluorescently-labeled cells were injected, an increase in the measured fluorescence signal due to the bolus of cells entering the blood stream was observed within seconds. This increase began to decay over the course of minutes, which, without being bound to any particular theory or mechanism, is believed to be due to dilution of the bolus of injected cells in the mouse blood volume. On top of the larger bolus, individual fluorescent spikes were detected which are consistent with brightly-labeled fluorescent cells passing through the instrument field of view. In additional experiments (data not shown) these spikes were observable up to 1 hour after injection. The average FWHM of the measured fluorescent spikes was about 0.23 sec, which corresponds to a linear flow speed inside the instrument field of view of approximately 4.5 mm/sec. This speed agrees well with reported literature values of average flow speeds in mice tail arteries of less than 8 cm/sec. Note that relatively small numbers of fluorescent spikes were observed here paradoxically because large numbers of cells were injected in these tests. This resulted primarily in a DC fluorescence increase as a result of the bolus as opposed to many individual spikes as in our phantom experiments.

In contrast, when unlabeled control cells were injected (FIG. 7b) neither the bolus nor individual fluorescent spikes were observed. The measured average background autofluorescence signal was similar in amplitude to that observed in the phantom. However, inspection of the data revealed that there was a small but consistent 1-2 Hz component in the signal which is attributed to artifacts from breathing movements of the mouse (this component was not present in the detected signal in flow phantom studies). While the amplitude of this signal component was significantly lower than the fluorescent signals from circulating cells, minimization of these motion artifacts—by carefully securing the tail—was nonetheless critical in these experiments.

Finally, note that for all experiments performed a steady decrease in the background signal of about 1% per minute was observed over the course of the experiment. The cause for this decrease is unclear but is believed to be due to a decrease in the core temperatures of the mice during the experiments and/or to photobleaching of native tissue chromophores.

Example 7: Tomographic Reconstruction of Single-Tube Flow Phantoms

As an initial test of the tomographic reconstruction capability of the DFFC instrument, a set of flow phantoms embedded with single strands of TYGON tubing were fabricated and tested. In this experiment and the following experiments, two laser excitation sources 120A, B were used as follows: The lasers were modulated at 10 Hz with a duty cycle of 50% and opposite phase as illustrated in FIG. 8. This modulation was controlled using two output channels of a multi-function data acquisition card (DAQ; NI-USB-6251, National Instruments, Austin, Tex.). The average power at the sample for both lasers was 7.5 mW with a spot size of 1 mm in diameter.

During experiments, photon count data was captured with the PMM-328 software (Boston Electronics). The photon counting threshold for each channel was −100 mV with a sampling rate of 100 samples/second. For each sample "run," 7500 data samples were collected so that the acquisition time was 75 seconds. Experimental runs could then be repeated an arbitrary number of times to allow for continuous data collection, and data from separate runs were concatenated during post-experimental signal processing. The start of each data acquisition cycle was triggered on the rising edge of laser 1 so that the lasers and MCS sampling times were synchronized. Since each data channel recorded signals when the lasers were sequentially illuminating, it was also necessary to parse the data after acquisition to generate 12 separate measurements for each of the source-detector pair combinations. This step was performed using custom-written code in MATLAB (The Mathworks, Natick, Mass.).

Except where noted, samples were run through flow phantoms at a constant linear flow rate of 1 cm/sec, which is similar to the upper limit of blood flow speeds reported in mouse tail veins. After data acquisition, the phantom was then rotated to different orientations with respect to the reference—specifically, 90, 180, 270, and 315 degrees—and data collection was repeated.

Example background-subtracted measured photon counts on the 6 detectors as a function of time when the first laser ("laser 1") was illuminating the sample are shown in FIGS. 9a-9f. An analogous data set was also simultaneously collected when laser 2 was illuminating the sample (not shown for brevity). When a fluorescent microsphere passed through the instrument field-of-view, a transient "spike" was recorded on all channels. In this particular experiment the flow tube of the phantom was oriented toward the bottom of the detector ring so that the tube was physically closest to detector 5. The difference in signal amplitude between each channel (i.e., the "spike heights") is evident, i.e., the signals from detectors 4-6 were the largest in magnitude. This difference in inter-channel signal intensity provided the basis for our ability to reconstruct cross-sectional fluorescence images.

Following data collection, tomographic image reconstructions were performed using custom-written MATLAB code. The data was first parsed into 12 different channels, corresponding to each of the (two) source and (six) detector pairs. Data was then re-summed into 0.1 s time bins, so that the overall effective sampling rate was 10 Hz. The intensities were calibrated for the (minor) differences in channel sensitivity. The mean background was then subtracted from each detection channel to remove DC background signals.

Two-dimensional images of the phantom or tail cross-section were then generated for each time-point using an approach commonly used in diffuse fluorescence tomography (DFT) and fluorescence mediated tomography (FMT). Specifically, a linear matrix equation of the form Wx=b was formed for each 0.1 sec timepoint. Here, b was the vector of 12 measurements collected during each sample interval (time point). The "weight functions" W were computed using a Monte Carlo (MC) simulation. For this, a modified MC code based on the publicly available code on the Oregon Medical Laser Center website as the inventors have described previously (see N. Valim, J. L. Brock and M. J. Niedre, "Experimental measurement of time-dependant photon scatter for diffuse optical tomography," J Biomed Opt 15(06), (2010) (the entirety of which is hereby incorporated by reference)). The 3 mm diameter medium was simulated with a 0.25×0.25 pixel size. Optical properties $\mu_s=150$ cm$^{-1}$, g=0.9 and $\mu_a=0.1$ cm$^{-1}$ were assumed. The number and path of photons emerging from the medium from an incident pencil beam at the detector locations were logged. In each case, 1 billion photons were tracked which required about 72 hours of computation time on a 3.2 GHz Dual-Core PC running Linux. Example weight functions between the first laser and detectors 1-3 are shown in FIGS. 9c-9e, respectively.

To solve this system of equations and obtain a fluorescence image, the 3 mm diameter cross-sectional tissue volume was discretized into a 250 μm grid. The fluorescence concentration at each point in the cross-section, x was then calculated at each time point using the randomized algebraic reconstruction technique (r-ART). For these experiments, a regularization parameter of $\lambda=0.25$ was used. A total of 25 iterations were performed since further iterations resulted in no observable changes to the reconstruction. The choice of r-ART for computation of the inverse problem was made because it is frequently used for DFT imaging, computes rapidly, and allows the solution to be constrained to non-negative values.

An example image obtained from a single fluorescent microsphere (spike), along with the white-light cross-sectional image of the phantom is shown in FIGS. 10a and 10b, respectively. As shown, the microsphere was reconstructed in a location close to the physical location of the TYGON tube. Although the spheres should in principle reconstruct as point objects, unsurprisingly the algorithm yielded images with a slightly extended ("blurry") shape with a full width at half maximum diameter of about 0.5 mm. Similar measurements and reconstructions were performed when the same phantom was rotated counterclockwise through 90°, 180°, 270° and 135°. Example image reconstructions for each of these orientations, along with white light cross-sectional photographs are shown in FIGS. 10c-j, respectively. In all cases the fluorescent microspheres were reconstructed in the approximate location of the tubing. In the particular case where the tube was oriented at 135° (i.e., closest to detector 1) the object was reconstructed as a more elongated source along the diagonal, however the centroid of the reconstructed object corresponded well to the location of the tube. The technique was also found to be robust in that the reconstructed position was consistent between individual spikes for each experiment. However, the reconstructed signal amplitudes varied by a factor of 2-3 from sphere to sphere, both due to variations in sphere brightness and variation in flow speeds in the parabolic flow profile.

As a test of the DFFC's ability to resolve depth information, another set of experiments was conducted in which the TYGON tubing was more centrally placed in the phantom cross-section. An example reconstruction where the tube was closest to the bottom right edge is shown in FIG. 10k, along with the reconstructed image as shown in FIG. 10l. In this case, the algorithm reconstructed a significantly more distributed source, the centroid of which was at the correct "clock position" of the tube but at the incorrect depth near edge of the phantom. These effects (i.e., distributed objects reconstructed near the edge of the phantom) were consistently observed in repeated experiments with deep-seated flow tubes. Without wishing to be bound to any theory, these effects were most likely due to the relatively small data sets and the under-determined nature of the reconstruction problem and, DFFC designs utilizing larger numbers of sources 120 (e.g. 3, 4, 5, 6 7, 8, 9 or 10 or more emission sources) and detectors 140 (e.g. 7, 8, 9, 10, 11, 12, 13, 14, 15, 16, 17, 18, 19, 20, or more optical fibers), for example, are believed likely to be more suitable to localizing signals originating deeper within tissue.

Example 8: Tomographic Reconstruction of Double-Tube Flow Phantoms

Another series of tests were conducted with double-tube flow phantoms that used a single length of TYGON tubing looped twice through the resin material. FIGS. 11a-b show sample data sets from a configuration in which two tubes were positioned on opposite sides of the phantom, close to the left and right edges. These data are the sum of the background-subtracted data from all six channels when laser 1 and laser 2 were illuminating the sample, respectively. A cross-sectional image of the cleaved phantom (obtained after DFFC data acquisition) is shown in FIG. 11c. Fluorescent spikes were detected in pairs separated by about 3 seconds, since each microsphere passed twice through the DFFC field-of-view, i.e. first along the left side and then right side of the phantom. In this case, the detected fluorescence amplitude for the first spike was significantly larger when laser 1 was illuminating the phantom (since it was directly illuminating the left flow tube) compared to laser 2, and the opposite was true for the second spike. Example reconstructed fluorescence images for two spikes (indicated by arrows in FIGS. 11a and 11b) are shown in FIGS. 11d and 11e, corresponding to the approximate locations of the left and right tubes.

Similarly, FIGS. 12a and 12b show the sum of acquired data on all six channels from the two lasers when the same phantom was rotated 90° counterclockwise so that the tubes were close to the bottom and top edges of the phantom (a cross-section of which is shown in FIG. 12c). As above, the spikes were detected in pairs, but the amplitude of the sum of the detected spikes was approximately the same when either laser was illuminating the sample (since the tubes were approximately equally far from the laser). Example reconstructed images for two spikes are shown in FIGS. 12d and 12e, respectively, again corresponding to the approximate locations of the top and bottom tubes.

Example 9: Tomographic Reconstruction of Quadruple-Tube Flow Phantoms

A series of experiments was also performed using phantoms with four flow channels embedded with two separate lengths of TYGON tubing that were looped twice each through the resin material. Although difficult to fabricate, these flow phantoms had approximately evenly spaced flow channels, with one close to each of the top, bottom, left and right edges, an arrangement that roughly mimics the location of the 4 major blood vessels in the mouse tail: the ventral artery, lateral and dorsal tail veins. FIGS. 13a and 13b show the sum of the detected signal on all 6 channels when each laser was illuminating the sample. The location of the four flow channels—denoted as tubes 1a, 1b, 2a and 2b—in the phantom cross-section are shown in the FIG. 13c. Again, the fluorescent spikes were detected in pairs as microsphere passed through the field-of-view twice on its return trip through either tube. Example image reconstructions for each of the four flow channels are shown in FIGS. 13d-13g. Note that lower flow rates (1 mm/sec) were used for these experiments; as such, the inter-spike arrival times were about 10 times longer than the case of the double-tube phantoms. Further, a range of 2-3 orders of magnitude in reconstructed intensities was observed as before, but generally values were approximately twice as large for the horizontally oriented flow tubes as for the vertically oriented tubes. This is believed to be due to differences in excitation light intensity near the left and right edges of the tube compared to the top and bottom edges. In principle the tomographic reconstruction should account for this intensity difference, but the effect was consistently observed. Again, this may be a result of the relatively limited tomographic imaging data sets. However, the experiments nevertheless demonstrate the ability of the DFFC instrument and image reconstruction algorithm to accurately localize fluorescent microspheres in multiple locations in the phantom cross-section.

Example 10: In-Vivo Tomographic Reconstructions

Figure 14G:
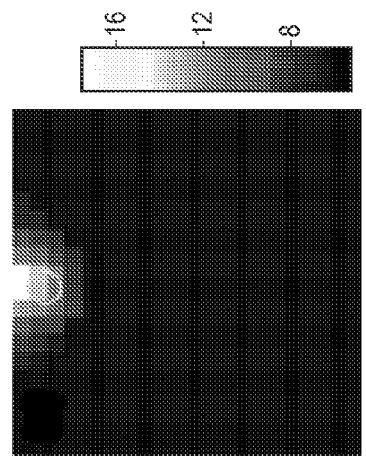
Figure 14F:
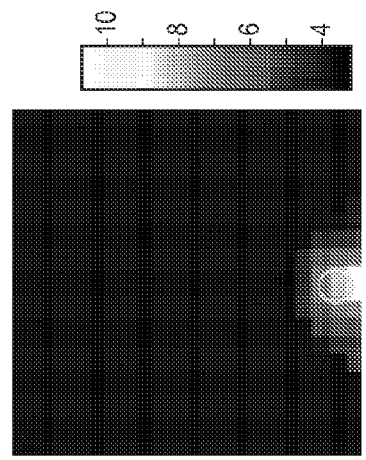
Figure 14E:
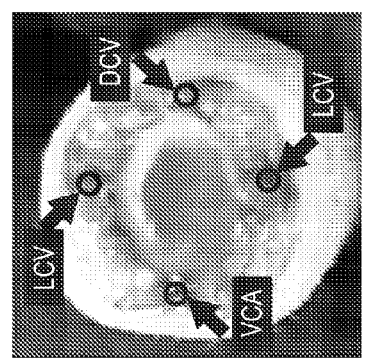
Figure 14J:
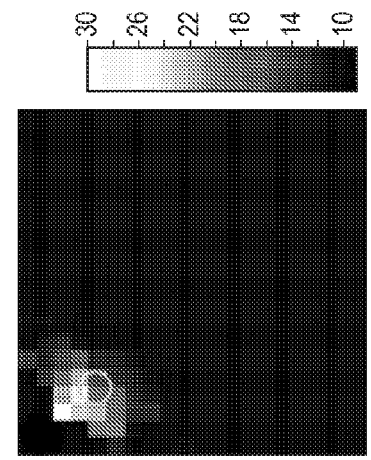
Figure 14I:
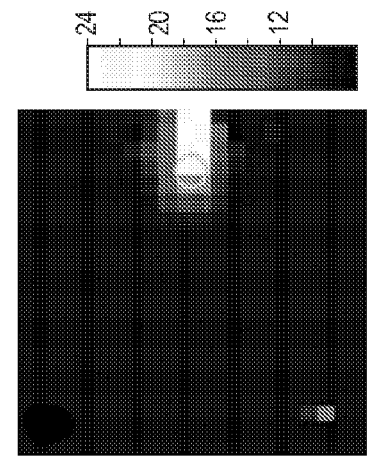
Figure 14H:
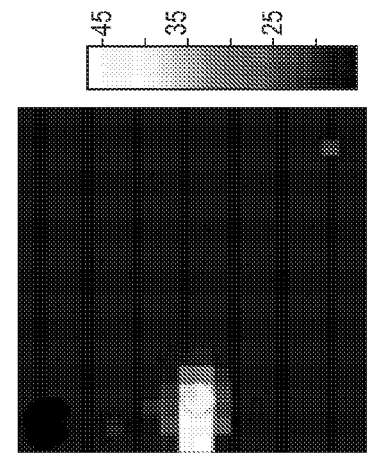

Finally, the in vivo tomographic imaging abilities of the DFFC instrument were assessed in nude mice with retro-orbitally injected multiple myeloma (MM) cells. Example data showing photon counts acquired over the first 15 minutes following injection (summed over all 6 detector channels) when laser 1 and laser 2 were illuminating the tail are shown in FIGS. 14a and b, respectively. In these figures, background subtraction was not performed so that the changes in the signal amplitude following injection could be observed (although subtraction was performed during image reconstruction). As reported previously, the DC increase in fluorescence intensity was measured immediately following the injection due to the bolus of cells entering the blood stream, overlaid with a series transient fluorescent spikes corresponding to circulating cells passing through the instrument field of view. This DC offset returned to baseline as the bolus was diluted by the blood volume. A cross-section of the tail (obtained after euthanizing the animal following injection of methylene blue) is shown in FIG. 14c, indicating the location of the ventral artery (VA), lateral veins (LV) and dorsal veins (DV). As noted above, the mouse was placed on its side during these experiments, so that the ventral artery (normally on the bottom side on the tail) was facing laser 1. Example reconstructed images for five selected spikes are shown in FIGS. 14d-14h. About two-thirds of the cells were reconstructed in approximately the left, right, top and bottom edges of the tail cross-section (FIGS. 14d-14g), and the remainder of the cells were reconstructed at intermittent angles as in FIG. 14h. Though it is impossible to directly verify the accuracy of image reconstructions following each experiment, the four positions identified in the reconstructions correspond to the approximate anatomical locations of the major blood vessels in the tail of the mouse (FIG. 14c). Since the cells were newly injected, it is reasonable to surmise that most of them were circulating through the major blood vessels. In addition, the average measured spike width was approximately 0.4 sec (full width at half maximum). Given the 0.7 mm field of view of the DFFC (20), this corresponds to a flow speed of approximately 0.3 cm/sec. Since the animal was under general anesthesia, this implies that the cells were moving in large, relatively fast-moving blood vessels. Finally, the studies in flow phantoms showed that the DFFC system is capable of accurately distinguishing between multiple circulating targets, further supporting the accuracy of the in vivo results.

Certain embodiments of the present invention have described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:
1. A diffuse fluorescence flow cytometer comprising:
a plurality of excitation sources adapted to be positioned circumferentially about a space sized for accommodating a limb of a subject, the limb comprising cells circulating therewithin, the cells being labeled with a fluorophore, wherein all of the excitation sources emit light having the same wavelength;
a plurality of detectors adapted to be positioned circumferentially about the space for (i) collecting a fluorescent emission from the cells generated in response to the light from each excitation source, and (ii) generating signals in response thereto, wherein-each of the detectors comprises an optical fiber having a first end angled toward the space;
a plurality of first bandpass filters, each of the first bandpass filters being (i) interposed between the space and one of the plurality of detectors and (ii) tuned to an emission peak of the fluorophore;
a plurality of second bandpass filters, each of the second bandpass filters being (i) interposed between the space and one of the excitation sources, and (ii) tuned to the same wavelength, the wavelength to which each of the second bandpass filters is tuned being different than a wavelength to which each of the first bandpass filters is tuned;
a multi-channel photomultiplier tube for receiving signals generated by the detectors from a second end of each of the optical fibers;
a preamplifier configured to (i) amplify the output of the photomultiplier tube, (ii) remove noise from the output of the photomultiplier tube, and (iii) remove a DC signal component from the output of the photomultiplier tube, the DC signal component arising from autofluorescence from the limb;
a photon counter for counting signals output by the preamplifier;
a memory; and
a processor responsive to the plurality of excitation sources and the plurality of detectors and configured to, in accordance with executable instructions stored in non-transitory form in the memory, generate, based on the signals generated by the plurality of detectors after the signals are received by the photomultiplier tube, amplified by the preamplifier, and counted by the photon counter, a tomographic reconstruction showing the position of the fluorescent emission within a cross-section of the limb,
wherein the processor is configured to, in accordance with the executable instructions:
operate the plurality of excitation sources to excite the fluorophore, thereby generating a fluorescent emission, wherein the plurality of excitation sources are operated to individually and sequentially illuminate the limb via emission of light theretoward, such that, for each of the excitation sources in turn, only one of the excitation sources illuminates the limb while all other excitation sources do not emit light, and
operate the plurality of detectors to detect the fluorophore within the limb via collection of the fluorescent emission, wherein the plurality of detectors are operated such that all of the detectors collect fluorescent emission during the sequential illumination by each of the excitation sources.

2. The diffuse fluorescence flow cytometer of claim 1, wherein the excitation sources are separated from one another by a fixed angular distance about the space.

3. The diffuse fluorescence flow cytometer of claim 1, wherein the detectors are separated from one another by a fixed angular distance about the space.

4. The diffuse fluorescence flow cytometer of claim 1, wherein the executable instructions include a timing waveform and a predetermined output intensity.

5. The diffuse fluorescence flow cytometer of claim 1, further comprising a plurality of third bandpass filters each interposed between the second end of an optical fiber and a channel of the multi-channel photomultiplier tube.

6. The diffuse fluorescence flow cytometer of claim 5, wherein each of the third bandpass filters is tuned to an emission peak of the fluorophore.

7. The diffuse fluorescence flow cytometer of claim 1, wherein the processor is configured to generate the tomographic reconstruction in accordance with the equation W·x=b wherein b is a vector of measurements collected at each of a plurality of time points and W is a weighting function.

8. The diffuse fluorescence flow cytometer of claim 1, wherein the processor is configured to compare the tomographic reconstruction of the location of the fluorescent emission with a cross-sectional image of the limb and verify that the fluorescent emission corresponds to a blood vessel.

9. The diffuse fluorescence flow cytometer of claim 1, wherein the space is insufficient to accommodate the entire subject.

10. The diffuse fluorescence flow cytometer of claim 1, wherein:
   the plurality of excitation sources are arranged in two rings each encircling the space; and
   the first ends of the optical fibers are angled to collect fluorescent emission in a single plane located between the rings.

11. The diffuse fluorescence flow cytometer of claim 1, further comprising a second detector positioned proximate the space for (i) collecting background autofluorescence not corresponding to the fluorescent emission from the cells generated in response to the light from each excitation source, and (ii) generating signals in response thereto, wherein (a) the second detector is coupled to a dedicated channel of the multi-channel photomultiplier tube, and (b) the dedicated channel is tuned to detect only the background autofluorescence.

12. The diffuse fluorescence flow cytometer of claim 11, wherein the processor is configured to, in accordance with the executable instructions, correct the tomographic reconstruction based on the background autofluorescence collected by the second detector.

13. The diffuse fluorescence flow cytometer of claim 1, wherein the processor is configured to, in accordance with the executable instructions, modulate each of the plurality of excitation sources at the same frequency.

* * * * *

UNITED STATES PATENT AND TRADEMARK OFFICE
CERTIFICATE OF CORRECTION

PATENT NO. : 9,968,259 B2  
APPLICATION NO. : 14/371850  
DATED : May 15, 2018  
INVENTOR(S) : Mark Niedre, Eric William Zettergren and Charles Lin Page 1 of 1

It is certified that error appears in the above-identified patent and that said Letters Patent is hereby corrected as shown below:

In the Specification

At Column 1, Line 15, insert the following heading and paragraph:
--GOVERNMENT SUPPORT
This invention was made with government support under Grant Number HL098750 awarded by the National Institutes of Health. The government has certain rights in the invention.--

Signed and Sealed this
Seventeenth Day of November, 2020

Andrei Iancu
*Director of the United States Patent and Trademark Office*